(12) United States Patent
Mizutani et al.

(10) Patent No.: US 7,686,793 B2
(45) Date of Patent: Mar. 30, 2010

(54) INTERLABIAL PAD AND WRAPPING BODY

(75) Inventors: Satoshi Mizutani, Kagawa (JP); Koichi Yamaki, Kagawa (JP); Yuki Noda, Kagawa (JP); Megumi Tokumoto, Kagawa (JP); Akane Sakai, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 0 days.

(21) Appl. No.: 10/706,303

(22) Filed: Nov. 10, 2003

(65) Prior Publication Data

US 2004/0147898 A1 Jul. 29, 2004

Related U.S. Application Data

(63) Continuation of application No. PCT/JP02/04886, filed on May 21, 2002.

(30) Foreign Application Priority Data

| May 22, 2001 | (JP) | ............................. 2001-152403 |
| Nov. 27, 2001 | (JP) | ............................. 2001-361463 |

(51) Int. Cl.
*A61F 13/45* (2006.01)
*A61F 13/26* (2006.01)
*A61F 13/34* (2006.01)
*A61F 13/20* (2006.01)

(52) U.S. Cl. ............................. 604/385.17; 604/385.03; 604/387

(58) Field of Classification Search ......... 604/327–329, 604/346–347, 355, 385.03, 385.08–385.09, 604/385.14, 385.17–385.19, 387
See application file for complete search history.

(56) References Cited

U.S. PATENT DOCUMENTS

| 2,097,033 | A | * | 10/1937 | Mcvittie | ..................... 604/286 |
| 2,300,001 | A | * | 10/1942 | Morando | ..................... 604/401 |
| 2,735,127 | A | * | 2/1956 | Parsons | ..................... 15/227 |
| 3,967,631 | A | * | 7/1976 | Kosal | ..................... 132/73 |
| 4,405,326 | A | * | 9/1983 | Lenaghan | ............... 604/385.31 |
| 4,595,392 | A | * | 6/1986 | Johnson et al. | ......... 604/385.17 |
| 5,320,531 | A | * | 6/1994 | Delizo-Madamba | ......... 433/136 |
| 5,336,208 | A | * | 8/1994 | Rosenbluth et al. | ......... 604/329 |
| D404,814 | S | * | 1/1999 | Mayer | ..................... D24/125 |

(Continued)

FOREIGN PATENT DOCUMENTS

EP 0888764 1/1999

(Continued)

OTHER PUBLICATIONS

Mizutani, et al., "Interlabial Pad", U.S. Appl. No. 10/705,406, Nov. 10, 2003.

(Continued)

*Primary Examiner*—Karin M Reichle
(74) *Attorney, Agent, or Firm*—Darby & Darby P.C.

(57) ABSTRACT

An interlabial pad is provided that can be easily worn in the interlabial space. A wrapping body is provided that contains the interlabial pad. In the interlabial pad, a finger insertion cavity is formed along the longitudinal direction of a back side sheet between a mini-sheet piece and the side opposite to body on the back side sheet. An opening of the finger insertion cavity for inserting a finger leads to a finger insertion restriction portion which farther restricts the insertion of the finger.

10 Claims, 16 Drawing Sheets

U.S. PATENT DOCUMENTS

| | | | |
|---|---|---|---|
| 5,868,727 | A | 2/1999 | Barr et al. |
| 5,891,126 | A | 4/1999 | Osborn, III et al. |
| 5,916,205 | A | 6/1999 | Olson et al. |
| 6,131,575 | A | 10/2000 | Lenker et al. |
| 6,131,736 | A | 10/2000 | Farris et al. |
| 6,156,323 | A * | 12/2000 | Verdicchio et al. ........... 424/401 |
| 6,358,235 | B1 * | 3/2002 | Osborn et al. .......... 604/385.18 |
| 6,647,549 | B2 * | 11/2003 | McDevitt et al. .................. 2/21 |
| 2002/0013566 | A1 * | 1/2002 | Chappell et al. ....... 604/385.13 |
| 2004/0019336 | A1 * | 1/2004 | Temple et al. ................ 604/294 |

FOREIGN PATENT DOCUMENTS

| | | | |
|---|---|---|---|
| FR | 2703244 A1 * | 10/1994 | |
| JP | 493722 | 1/1974 | |
| JP | 61108258 | 7/1986 | |
| JP | 63260556 | 10/1988 | |
| JP | 0356366 | 3/1991 | |
| JP | 05237151 | 9/1993 | |
| JP | 05293138 | 11/1993 | |
| JP | 6-506368 A1 | 7/1994 | |
| JP | 0640203 | 10/1994 | |
| JP | 08-215242 A1 | 8/1996 | |
| JP | 2000-051267 | 12/1999 | |
| JP | 2000501322 | 2/2000 | |
| JP | 2001506170 | 5/2001 | |
| JP | 2001-509402 | 7/2001 | |
| JP | 2002/513633 | 5/2002 | |
| JP | 02534163 | 10/2002 | |
| TW | 247431 A1 | 5/1995 | |
| TW | 294591 A1 | 1/1997 | |
| TW | 338315 A1 | 8/1998 | |
| TW | 416847 A1 | 1/2000 | |
| TW | 386030 A1 | 4/2000 | |
| TW | 386873 A1 | 4/2000 | |
| TW | 394681 A1 | 6/2000 | |
| TW | 442278 A1 | 6/2001 | |
| TW | 450802 A1 | 8/2001 | |
| TW | 454503 A1 | 9/2001 | |
| TW | 470640 A1 | 1/2002 | |
| TW | 524677 A1 | 3/2003 | |
| WO | 92/11825 | 7/1992 | |
| WO | 95/00094 A1 | 1/1995 | |
| WO | 95/17148 A2 | 6/1995 | |
| WO | WO 9602217 A1 * | 2/1996 | |
| WO | WO-98/08475 A1 | 3/1998 | |
| WO | WO-98/57610 A1 | 12/1998 | |
| WO | WO-99/01093 A1 | 1/1999 | |
| WO | WO-99/01096 A1 | 1/1999 | |
| WO | WO-99/26575 A1 | 6/1999 | |
| WO | 99/56681 | 11/1999 | |
| WO | WO-99/57610 | 11/1999 | |
| WO | 0040192 | 7/2000 | |
| WO | WO 0040197 A1 * | 7/2000 | |
| WO | 01/47458 A1 | 7/2001 | |

OTHER PUBLICATIONS

Mizutani, et al., "Interlabial Pad", U.S. Appl. No. 10/705,408, Nov. 10, 2003.

Mizutani, et al., "Interlabial Pad", U.S. Appl. No. 10/705,780, Nov. 10, 2003.

Mizutani, et al., "Interlabial Pad and Package Thereof", U.S. Appl. No. 10/705,404, Nov. 10, 2003.

Mizutani, et al., "Interlabial Pad", U.S. Appl. No. 10/705,407, Nov. 10, 2003.

Mizutani, et al., "Interlabial Pad", U.S. Appl. No. 10/705,403, Nov. 10, 2003.

Mizutani, et al., "Individual Packaging Body and Outer Vessel Therefor", U.S. Appl. No. 10/705,402, Nov. 10, 2003.

Mizutani, et at, "Interlabial Pad Individual Packaging Vessel, and Individual Packaging Body", U.S. Appl. No. 10/705,781, Nov. 10, 2003.

Mizutani, et al., "Interlabial Pad", U.S. Appl. No. 10/705,399, Nov. 10, 2003.

Mizutani, et al., "Interlabial Pad", U.S. Appl. No. 10/705,812, Nov. 10, 2003.

Mizutanl, et al., "Interlabial Pad", U.S. Appl. No. 10/705,811, Nov. 10, 2003.

Mizutani, et al., "Interlabial Pad Individual Packaging Body", U.S. Appl. No. 10/705,669, Nov. 10, 2003.

Mizutani, et al., "Interlabial Pad and Package Thereof", U.S. Appl. No. 10/705,400, Nov. 10, 2003.

Mizutani, et al., "Interlabial Pad", U.S. Appl. No. 10/705,778, Nov. 10, 2003.

Mizutani, et al., "Interlabial Pad Individual Packaging Vessel", U.S. Appl. No. 10/705,673, Nov. 10, 2003.

Mizutani, Satoshi, "Interlabial Product Having Form for Finger Securement, and Individual Package", U.S. Appl. No. 10/705,779, Nov. 10, 2003.

Mizutani, et al., "Interlabial Pad and Package Thereof", U.S. Appl. No. 10/705,810, Nov. 10, 2003.

Mizutani, et al., "Flap-Equipped Interlabial Pad", U.S. Appl. No. 10/705,670, Nov. 10, 2003.

* cited by examiner (A)

(B)

(C)

INTERLABIAL PAD AND WRAPPING BODY

CROSS-REFERENCE TO RELATED APPLICATIONS

This application is a Continuation of International Application No. PCT/JP02/04886 filed May 21, 2002, which application published in Japanese on Nov. 28, 2002 as WO 02/094150 A1 under PCT Article 21(2).

BACKGROUND OF THE INVENTION

1. Technical Field

The present invention relates to an interlabial pad which can be easily worn to the interlabial space with precision and a wrapping body for wrapping the interlabial pad with a wrapping container.

2. Background Art

Conventionally, a sanitary napkin and a tampon are used generally as female sanitary products. Here, there have been great efforts to prevent the leak of menstrual blood from gap caused by poor adhesion near the ostium vaginae as for the sanitary napkin. Moreover, as for the tampon, there have been great efforts for relieving the foreign feeling and the discomfort when wearing the sanitary products and intervaginal wearing trouble due to the nature of those products.

Under such situation, sanitary products of the interlabial pad have attracted people as a sanitary product positioned between the sanitary napkin and the tampon in recent years.

The interlabial pad, fixed by inserting it between the labia, has characteristics that it is difficult to cause the leak of menstrual blood because of higher adhesion to the body than that of the sanitary napkin and psychological resistance thereof on wearing is lower than that of the tampon which is inserted into the vagina.

However, interlabial pads have a drawback that it is more difficult to wear them than sanitary napkins because interlabial pads are wrapped in the interlabial space whose visual check is difficult. Further, if an interlabial pad is not worn to an appropriate point, menstrual blood leakage results in immense damage because the interlabial pad is smaller than the sanitary napkin. Furthermore, the interlabial pad is more likely to be mis-worn than the tampon.

With regard to the present inventions for dissolving wearing troubles in interlabial pads, PCT International Publication No. WO99/56689 discloses a pad having a structure that a projection is formed on the opposite side to the body-contacting surface. With this structure, a wearer can wear a pad by taking the projection with fingers. It is supposed that that this kind of pad can be worn more readily than a pad without a projection. (refer to FIG. 31)

It is required to take the projection of a pad with at least two fingers such as a thumb, a forefinger or others for wearing such a interlabial pad. So, balls of fingers (fingerprint sides) having a fineness of perception are used to take the projection and positioned on the side face of the projection. More specifically, the wearer should detect the wearing point with the tips of her nails when fixing an interlabial pad. So, actually, a wearer should trust her intuition and it is rather difficult for her to detect an appropriate wearing point. Especially, females often let their nails grow long or wear artificial nails. So, in some cases, it is almost impossible to fix conventional interlabial pads shown above to an appropriate point.

As just described, easy wearing through correct detection of a wearing point, reduction of mis-wearing and sufficient adhesion onto the pubic region have not been realized by the conventional interlabial pads shown above. Further, there are still cases where menstrual blood adheres to fingertips when fixing a pad, causing psychological oppositions to use an interlabial pad.

Furthermore, conventional interlabial pads shown above are likely to be misaligned to the interlabial space because the position of fingers to take pads is not stable, resulting in a risk of mis-wearing.

SUMMARY OF THE INVENTION

The present invention has been made to solve the problems shown above. An object of the present invention is to provide an interlabial pad with a structure that is capable of wearing the pad securely and sanitarily within the interlabial space of females.

The above objects can be attained, according to the present invention, by an interlabial pad that is fixed in such a way that it contacts the pubic region by using a ball of a finger to check the fixing point, more specifically, a structure having a finger insertion cavity into which a finger can be inserted while contacting a side of an interlabial pad opposite to the body is provided, and a restriction to prevent further insertion of a finger is provided in the finger insertion cavity at a position which permits fixing stably and smoothly the interlabial pad in the interlabial space.

More specifically, the present invention provides the following features:

(1) An interlabial pad capable of absorbent body fluid formed into a substantial rectangle having a longitudinal direction and a lateral direction provided with a size, weight and flexibility allowing to be pinched and held in between the labia without forcing, comprising a body side face orientated to the body side and an opposite side face to body orientated to a garment side, wherein the interlabial pad has a finger insertion cavity, formed along the longitudinal direction on said opposite side face to body, for inserting a finger of the wearer, and an opening portion of the finger insertion cavity constitutes a finger insertion opening for directly securing an opening in the fingerbreadth direction in the planar direction of said opposite side face to body;

said finger insertion opening serves to guide the fingertip of the wearer to a portion (finger application point) of said opposite side face to body corresponding to an area (application point) of said body side face applied to a predetermined position between the labia of the wearer; and a finger insertion restriction portion for restricting the advance of the insertion of the finger from said finger insertion opening in said finger insertion cavity, is provided in the vicinity of said finger application point.

According to the invention (1) shown above, a finger insertion cavity to which a finger can be inserted is provided on the side of an interlabial pad opposite to body. In the finger insertion cavity, a finger insertion restriction portion is provided as a stopper to prevent the insertion of a finger at a specified position. Therefore, the progress of a finger inserted from the finger insertion opening to the finger insertion cavity stops and the finger stays constantly at a position where the finger insertion restriction portion is provided in the finger insertion cavity when a wearer fixes an interlabial pad by putting a ball of a finger on the side of the interlabial pad opposite to body in the longitudinal direction. So, a positional relationship between a ball of a finger (a fingerprint side) at a top joint that is most sensitive and the longitudinal direction of an interlabial pad is recreated stably in any wearer.

The finger insertion restriction portion is provided at a place of the interlabial pad so that a ball of finger inserted into the finger insertion cavity stays there and pushes open a pair of the labia through the interlabial pad to detect the ostium vaginae that is situated in the back of the interlabial space. So, any wearer can detect the ostium vaginae easily. Therefore, the interlabial pad can be fixed to an appropriate position inside of the labia that is hardly visible.

In this specification, "finger breadth directions" denotes a direction other than the direction of finger thickness, specifically, it denotes the direction of nail width. "Opening of finger breadth" denotes an opening having an enough size to insert a finger.

Also in this specification, "directed" denotes that something is aligned to a specified direction.

In this specification, a "front end" of the interlabial pad denotes an end that is located at the clitoral side (referred to as the "front side" hereafter) when the pad is fixed. A "rear end" of the interlabial pad denotes an end that is located at the analis side (referred to as the "rear side" hereafter) when the pad is fixed.

(2) The interlabial pad according to (1), comprising: a mini sheet piece disposed in a way to stride from one side to the other side taking the longitudinal direction of said interlabial pad as a central axis, on the opposite side face to body of said interlabial pad, wherein: said finger insertion opening is formed between the mini sheet piece and said opposite side face to body.

According to the invention (2), a mini sheet piece is attached to the side of an interlabial pad opposite to body. With a simple configuration that the mini sheet piece is provided, a finger insertion cavity is formed to make fixing of the interlabial pad easier-by wearing the interlabial pad on a tip of a finger.

In the interlabial pad with such a mini sheet piece, the mini sheet piece is preferably provided at a position from the middle to the rear end of the interlabial pad in the longitudinal direction. By this, a ball of a finger in the top joint is made to contact the rear side of the interlabial pad opposite to body. Menstrual blood has a property that it is discharged from the ostium vaginae situated in the rear side of the labia and flows to the front side of the labia due to the wettability of the mucus inside of the labia. In the present invention, menstrual blood discharged from the ostium vaginae can be absorbed instantly by making the rear side of the interlabial pad contact the ostium vaginae. Menstrual blood that flows into the front side of the labia is absorbed securely with the vicinity of the front end of the interlabial pad in contact with the front side of the labia and the side of the interlabial pad in contact with external genitals by being pinched with labia and folded.

(3) The interlabial pad according to (1) or (2), wherein said finger insertion restriction portion is formed as a portion where a part of said finger insertion cavity is made narrow.

According to the invention (3) shown above, the finger insertion restriction portion is formed so that the progress of inserting a finger is physically impossible by making the width in the lateral direction thereof on the opposite side to the body side smaller than the width of a finger. Consequently, not only the insertion of a finger but also the positional relationship between a finger in the finger insertion restriction portion and the lateral direction of the interlabial pad are restricted reducing the displacement between the interlabial pad and the labia in the lateral direction to make fixing of the interlabial pad more accurate.

(4) The interlabial pad according to any one of (1) to (3), wherein said finger insertion restriction portion is formed by binding said opposite side face to body each other.

According to the invention (4) shown above, the finger insertion restriction portion is formed by bonding areas on the opposite side to the body side and those are facing each other when the interlabial pad is folded. So, a long convex area that is convexly curved towards the body face side is formed in the longitudinal direction at the body face side near the finger insertion restriction portion.

By this, a wearer can fit the long convex area deeply into the back of the labia to prevent the occurrence of a gap between the interlabial pad and the labia.

In an area corresponding to the finger insertion restriction portion, even if a finger is inserted into the finger insertion opening, the state of narrowed width at the top of the long convex area where the interlabial pad is folded and maintained as it is. So, the top portion can be a starting point to insert the long convex area into a position near the ostium vaginae. A wearer can tightly fit the top of the long convex area into the ostium vaginae that is situated in the penetralia of the interlabial space (vestibule) using a ball of a finger in the top joint inserted in the finger insertion opening through the interlabial pad.

Further, a ball of a finger contacts the position corresponding to the top of the long convex area in the finger insertion opening formed inside of the long convex area. Consequently, the interlabial pad can be fixed by moving the long convex area along the vulva slit using a ball of a finger when fixing the interlabial pad.

In addition, since the long convex area is formed by folding the interlabial pad, it is deformed according to the shape of a finger inserted into the finger insertion opening formed inside of a part of the longer convex area when fixing the interlabial pad. However, when a finger is pulled out, it can be transformed according to the shape between the labia. As the result, the body face side of the interlabial pad can be tightly fixed to inside of the labia when fixing an interlabial pad in spite of the shape differences of the labia of wearers.

(5) The interlabial pad according to any one of (1) to (4), wherein a width dimension in said lateral direction of said finger insertion cavity is formed to reduce gradually from said finger insertion opening to said finger insertion restriction portion.

According to the invention (5) shown above, said finger insertion opening is formed in such a way that it gets smaller gradually from said finger insertion opening (largest) to said finger insertion restriction portion (smallest). Consequently, a finger inserted along inside of the opposite side to the body side from the finger insertion opening to the finger insertion opening is guided gradually and smoothly into the finger insertion restriction portion. As the result, accidents such as a break of a sheet provided at the opposite side of body by movement of a finger inserted into the finger insertion opening or a poor bonding between the opposite side to the body side and the mini sheet piece can be prevented.

(6) The interlabial pad according to any one of (1) to (5), wherein a interval dimension of said finger insertion opening and the finger insertion restriction portion is 10% to 80% of the length dimension in the longitudinal direction of said opposite side face to body.

According to the invention (6) shown above, the finger insertion opening is provided at the position 20% to 50% from the front end of an interlabial pad. The finger insertion restriction portion is positioned 60% to 100% from the front end of the interlabial pad. So, the interval between the finger insertion opening and the finger insertion restriction portion in the longitudinal direction falls under the range from 10 to 80% of the longitudinal dimension of the interlabial pad.

As described above, since the interval from the finger insertion opening to the finger insertion restriction portion is 10% or more to the longitudinal dimension of the interlabial pad, a finger inserted into the finger insertion opening is not likely to come out from the finger insertion opening resulting in reliable retention of a finger against the interlabial pad. Consequently, displacement of a finger in the finger insertion opening is prevented resulting in avoiding positional displacement against the labia when fixing the interlabial pad.

Since the interval dimension from the finger insertion opening to the finger insertion restriction portion is 80% or less of the longitudinal dimension of the interlabial pad, the mini sheet piece does not prevent a finger from pulling out from the finger insertion opening after fixing the interlabial pad. So, a finger can be pulled out smoothly, and positional displacement of the interlabial pad caused by the contact between the opposite side to the body side of the interlabial pad and a finger can be reduced.

(7) The interlabial pad according to any one of (1) to (6), wherein said finger insertion restriction portion is formed to position near one end edge in the longitudinal direction of said opposite side face to body.

According to the invention (7) shown above, the finger insertion restriction portion is formed at the position near the one end of the opposite side to the body side. So, since a ball of a finger in the top joint is positioned at the rear side of the interlabial pad, the ostium vaginae positioned at the rear side of the interlabial space can be detected more easily when a finger is inserted to the finger insertion restriction portion at the end of the finger insertion opening.

(8) The interlabial pad according to any one of (1) to (7), wherein a fingertip exit for protruding the nail tip of the inserted finger is formed, in said finger insertion restriction portion.

According to invention (8), a "nail tip escapement" is formed with an enough size that a nail of a finger inserted into the finger insertion opening can protrude. By this, even a wearer with longer nails or fake nails can securely guide a fingertip to the finger insertion restriction portion by sticking out the nail. As the result, a ball of a finger in the top joint can contact the side of the interlabial pad opposite to body more tightly. It can reduce the trouble that the ostium vaginae is not detected by a fingertip from the side of interlabial pad opposite to body in the finger insertion opening.

(9) The interlabial pad according to any one of (1) to (8), wherein said finger insertion restriction portion is formed at a position biased to the center thereof by a predetermined dimension in the longitudinal direction from one end edge in the longitudinal direction of said opposite side face to body.

According to the invention (9), the finger insertion restriction portion is provided at the position to the center, not the rear end of the interlabial pad. So, the interlabial pad covers a fingertip like a hood (refer to FIG. 8) and makes a wearer detect the position of the ostium vaginae using whole surface of a finger ball in the top joint including the fingertip. Consequently, a wearer can detect the ostium vaginae easily and fix the interlabial pad to an appropriate position more securely.

Also with the present invention, adhesion of menstrual blood not only to a finger inserted into the finger insertion opening but also a nail sticking out from the nail tip escapement can be prevented since the interlabial pad covers a nail protruding from the nail tip escapement.

(10) The interlabial pad according to any one of (1) to (9), wherein a finger insertion compulsory portion is formed for tilting compulsorily the finger insertion direction to the opposite side face to body toward said finger insertion restriction portion in said finger insertion cavity.

According to the invention (10) shown above, insertion direction of a finger is forced to slant in the direction of opposite side to the-body side due to the finger insertion direction forcing portion in the process of inserting a finger from the finger insertion opening into the finger insertion opening when fixing an interlabial pad. Consequently, a ball of a finger in the top joint can be fit to the opposite side to the body side more securely at the point when the fingertip reached the finger insertion restriction portion and the position of the ostium vaginae can be detected by a ball of a finger through each sheet and absorbent body more securely.

(11) The interlabial pad of claim (10), wherein said finger insertion compulsory portion is formed by the shape of folding of said mini sheet piece into said finger insertion cavity.

According to the invention (11) shown above, a part of the mini sheet piece is folded in the finger insertion opening in such a way that the interval between the mini sheet and said back side sheet decreases gradually. So, a finger is inserted in such a way that the outside of a finger (nail side) touches the mini sheet piece whose distance dimension against the opposite side of body decreases gradually starting from the finger insertion opening in the process of inserting a finger from the finger insertion opening into the finger insertion opening when fixing the interlabial pad. Consequently, a fingertip (tip of a nail) can be guided to the finger insertion restriction portion more smoothly. As the result, accidents such as a break of the opposite side to the body side by movement of a finger inserted into the finger insertion opening or poor bonding between the opposite side to the body side and the mini sheet piece can be prevented.

(12) The interlabial pad according to any one of claims (1) to (11), wherein the interlabial pad is used together with a sanitary napkin.

According to the invention (12), the interlabial pad and a sanitary napkin can be used at the same time. Some women use several napkins layered when an amount of menstrual blood is large. However, there were problems such as bulky feeling, outer appearance change. In addition, sanitary napkins are layered on areas other than a vicinity of the ostium vaginae where layered pads are not required resulting rash, excessive humidity. In this respect, with the interlabial pad according to the present invention, sanitary products are layered only on the labia and their vicinity having little effect on wear feeling and outer appearance, and in addition, occurrence of excessive humidity and rash around hips can be reduced. Further, it becomes possible that only the interlabial pads according to the present invention are changed without replacing sanitary napkins. A wearer does not have to carry auxiliary sanitary napkins that have a conspicuous size. Sanitary napkins here may include not only napkins sold as products for absorbing menstrual blood but also vaginal discharge absorbing sheets.

(13) The interlabial pad according to any one of (1) to (12), wherein said interlabial pad is a pad for incontinence of urine.

According to the invention (13) shown above, the pad can be used for incontinence absorb pad. That is ostium vaginae where the menstrual blood is discharged and a urethral meatus where urine is discharged locate between labia, and the interlabial pad of the present invention to be used between labia can absorb urine also.

As described hereinbefore, the pad of the invention can absorb urine around labia, especially around the urethral meatus and is useful for the absorbing pad for incontinence, especially for a light incontinence.

(14) The interlabial pad according to any one of (1) to (12), wherein said interlabial pad is a pad for absorbing vaginal discharge.

According to the invention (14) shown above, the interlabial pad can be used as a pad for absorbing the vaginal discharge. The interlabial pad is used between labia and can absorb the excretion other than the menstrual blood from ostium vaginae for the use therefore (for absorbing the vaginal discharge).

As described above, the pad can absorb the vaginal discharge in order to decrease the discomfort for the person, and is useful for the user who is not menstruating.

(15) A wrapping body comprising the interlabial pad according to any one of (1) to (14) and a wrapping container containing this interlabial pad, wherein said interlabial pad is contained by folding so that said finger insertion opening opens when said wrapping container is unwrapped.

According to the present invention (15) shown above, since the interlabial pad is contained in a wrapping container in such a way that the finger insertion opening is opened when the wrapping container is unsealed, a wearer can insert a finger into the finger insertion opening quickly and smoothly. Consequently, operation to fix the interlabial pad fixing becomes easier.

(16) The wrapping body according to (15), wherein said wrapping container is provided with a mark indicating the unwrapping direction identical to the insertion direction of the finger into said finger insertion opening.

According to the prevention (16) shown above, a wearer can know the unsealing direction to expose the finger insertion opening without opening the wrapping container. Consequently, it prevents a wearer from mistaking an unsealing direction. It also makes the direction to unseal the wrapping container and the direction to insert a finger into the finger insertion opening always aligned.

Further, the finger insertion opening will appear according to the unsealing operation where the wrapping container is unsealed from the near side of a wearer. In this state, a finger can be easily inserted into the finger insertion opening.

(17) The wrapping body according to (16), wherein said mini sheet piece in said interlabial pad is folded outward in a shape swelling toward the body side.

According to the invention (17) shown above, the finger insertion opening will naturally open since the folded mini sheet piece returns to the original shape when the wrapping container is unsealed. So, a wearer can easily know the position to which a finger is inserted and can insert a finger into the finger insertion opening more quickly and smoothly.

DETAILED DESCRIPTION OF THE INVENTION

An example of the present invention will now be explained referring to drawings. The present invention is not limited to the embodiment.

[Overall Structure of the Interlabial Pad]

Figure 1:
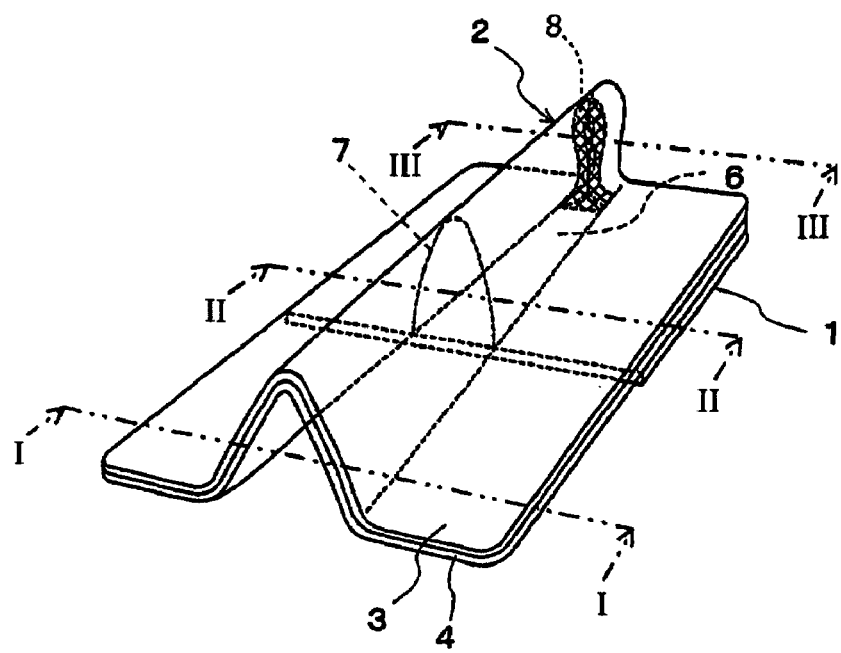
FIG. 1 is a perspective view of an interlabial pad according to the example of the present invention.
Figure 2:
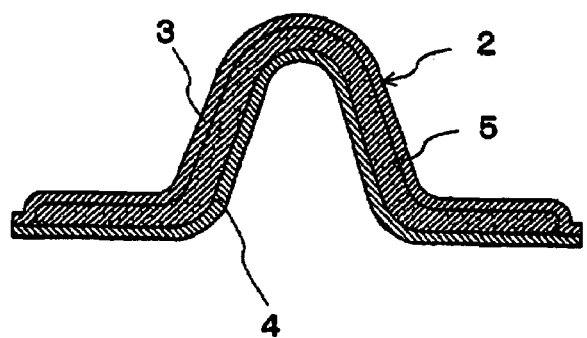
FIG. 2 is a cross section diagram in I-I view of the interlabial pad shown in FIG. 1 according to the example of the present invention.
Figure 3:
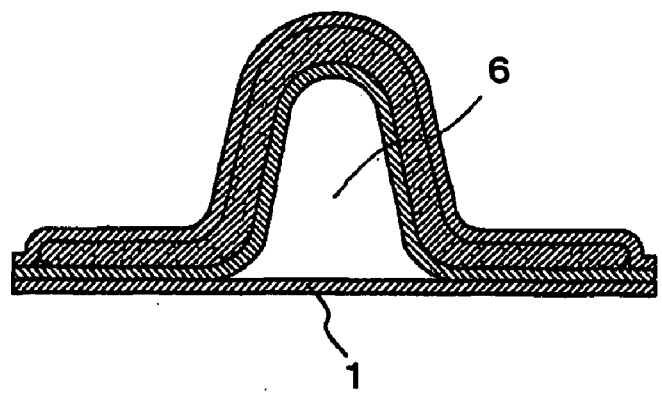
FIG. 3 is a cross section diagram in II-II view of the interlabial pad shown in FIG. 1 according to the example of the present invention.
Figure 4:
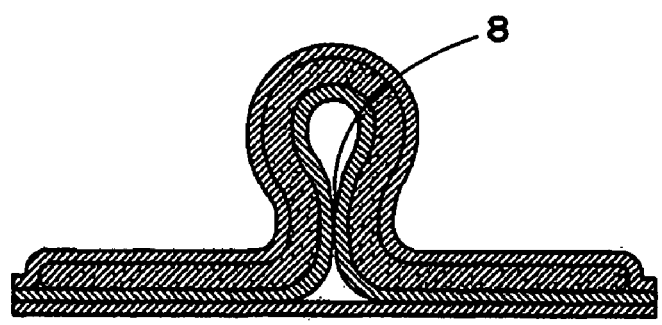
FIG. 4 is a cross section diagram in III-III view of the interlabial pad shown in FIG. 1 according to the example of the present invention.

Basic structure of the interlabial pad according to the example of the present invention will now be explained. FIG. 1 is a perspective view of the interlabial pad according to the example. FIG. 2 is a cross sectional diagram of a cross section I-I of the interlabial pad in FIG. 1 according to the example. FIG. 3 is a cross sectional diagram of a cross section II-II of the interlabial pad in FIG. 1 according to the example. FIG. 4 is a cross sectional diagram of a cross section III-III of the interlabial pad in FIG. 1 according to the example.

The interlabial pad according to the example has a long and thin shape as shown in FIG. 1 having a body-facing side that faces body and an opposite side to the body side that faces garments. A mini sheet 1 is fixed on the opposite side to the body side in such a manner opposed sides along the longitudinal axis of the interlabial pad are bridged. As shown in FIG. 2, this interlabial pad has a structure comprising an absorbent body 5 wherein a water permeable surface side sheet 3 facing the body and a water permeable or water impermeable back side sheet 4 facing the side opposite to body absorb body fluid.

The interlabial pad according to the example has a shape of substantial rectangle in plan. However, the shape is not particularly limited so far as it can be pinched and retained between the labia of elliptic shape, gourd-shape, drop-shape, etc.

On the body-facing side of the interlabial pad, as shown in FIG. 1, a long convex area 2 bulging towards the body-facing side is formed, at almost center of the lateral direction, along the longitudinal direction thereof. As shown in FIG. 3, a finger insertion opening 6 with a cross sectional view of chevron shape where a finger can be inserted is formed between the long convex area 2 and the mini sheet piece 1.

As shown in FIG. 1, this finger insertion opening 6 has an opening 7 near the center along the longitudinal direction of the interlabial pad. This opening forms the finger insertion opening where an opening in the direction of finger width is directly secure. In the meantime, the finger insertion restriction portion 8 is provided forming a stopper to restrict the progress of finger insertion to be the end of the finger insertion opening 6. In the interlabial pad, the cross section area of the substantial chevron shaped space formed inside of the long convex area 2 is reduced gradually along the longitudinal direction. The cross section area is reduced approximately as that of a finger at the opening 7 situated near the center of the longitudinal direction. Further, the cross section area is reduced at the finger insertion restriction portion 8 along the longitudinal direction so that the sides opposite to body on the back side sheet 4 are bonded to each other as shown in FIG. 4.

As described above, the finger insertion opening 6 is formed in such a way that the width dimension along the lateral direction decreases gradually towards the finger insertion restriction portion 8 starting from the opening 7. So, a fingertip in the lateral direction of the side opposite to body is guided to the finger insertion restriction portion 8 gradually and smoothly only by inserting a finger from the opening 7 to the finger insertion opening 6 along the inside of the side opposite to body. Consequently, breaks, etc of the sheet provided on the side opposite to body due to the finger insertion action into the finger insertion opening 6 can be prevented.

[Wearing Condition]

Figure 5:
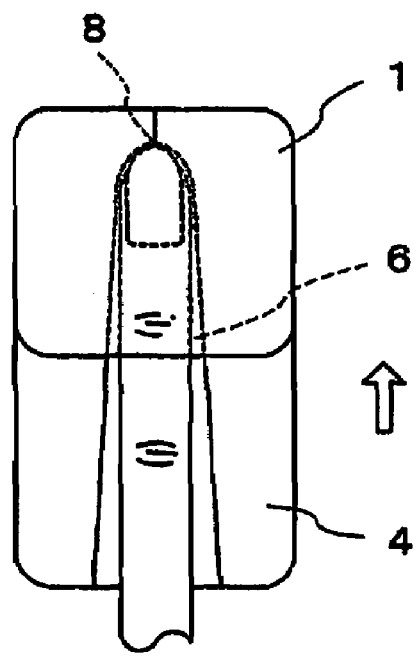
FIG. 5 is a schematic plane view indicating the state of a finger in dotted lines when a wearer inserted a finger into the finger insertion opening using the interlabial pad according to the example of the present invention.
Figure 6:
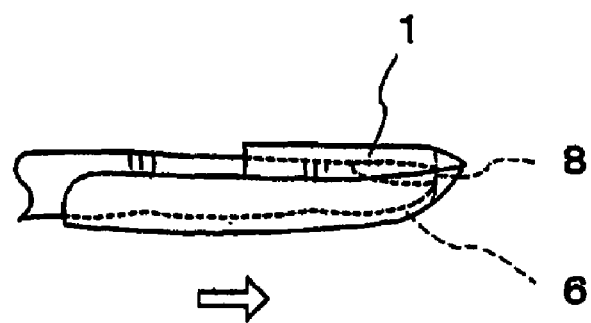
FIG. 6 is a schematic side view indicating the state of a finger in dotted lines when a wearer inserted a finger into the finger insertion opening using the interlabial pad according to the example of the present invention.
Figure 7:
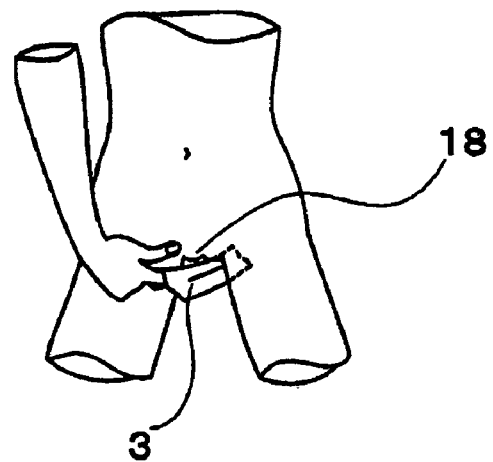
FIG. 7 is a schematic diagram to explain the state that the interlabial pad is fixed to the interlabial space according to the example of the present invention.
Figure 8:
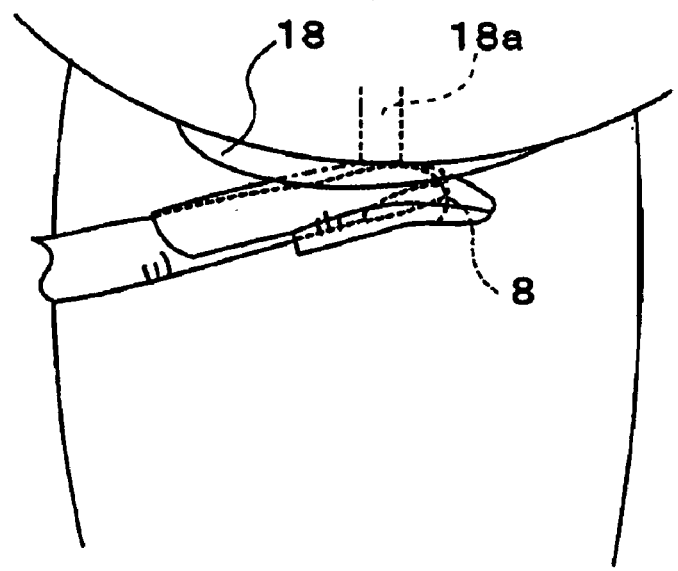
FIG. 8 is a schematic diagram to explain the state that the interlabial pad according to the example of the present invention is fixed to the interlabial space, indicating the state that the interlabial pad is pinched at the specified position of the interlabial space with a finger inserted into the finger insertion restriction portion.
Figure 9:
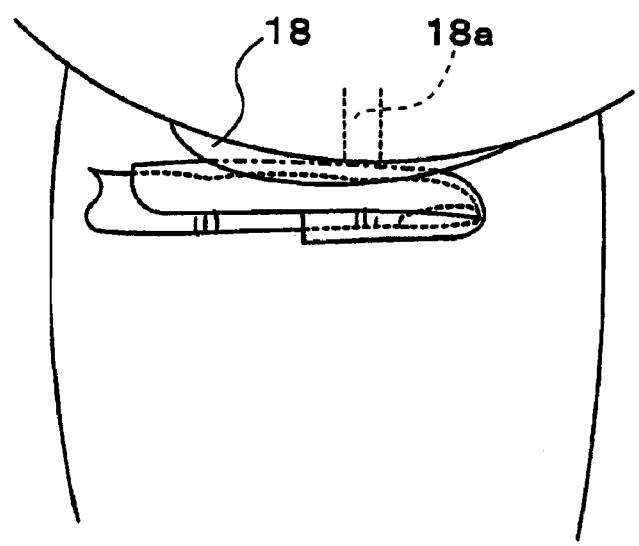
FIG. 9 is a schematic diagram to explain the state that the interlabial pad without the finger inserting restriction portion is fixed to the interlabial space.

Wearing condition of the interlabial pad according to the example will now be explained. FIG. 5 is a schematic plane view showing the state that a finger is inserted into the finger insertion opening 6 of the interlabial pad according to the example. FIG. 6 is a schematic side view of the state that a finger is inserted into the finger insertion opening 6 of the interlabial pad according to the example. FIG. 7 is a schematic diagram to explain the state that the interlabial pad according to the example is fixed to the labia 18. FIG. 8 is a schematic diagram to explain the state that the ostium vaginae 18a is detected by a finger inserted in the finger insertion opening 6 of the interlabial pad according to the example. FIG. 9 is a schematic diagram to explain the state that the ostium vaginae 18a is detected by a finger inserted in the finger insertion opening of an interlabial pad without the finger insertion restriction portion.

The interlabial pad according to the example should be fixed to a fingertip before using the interlabial pad. Wearing to a fingertip is performed by inserting a finger into the finger insertion opening 6 from the finger insertion opening 7. In this case, as shown in FIGS. 5 and 6, a finger of a wearer is inserted to the position up to the finger insertion restriction 8 along the arrow direction in the figures. However, the fingertip does not protrude out of the interlabial pad due to the finger insertion restriction portion 8 and stable insertion state of the finger is maintained.

As shown in FIG. 7, the interlabial pad according to the example is worn to the labia 18 from the front side of body. In this fixing action, as shown in FIG. 8, the ostium vaginae 18a is detected keeping the body face side of the surface side sheet 3 in touch with the labia 18 and the interlabial pad is pinched with the orientation unchanged, then, the interlabial pad is fixed to the most appropriate position between the labia 18 having a concaved shape.

On the other hand, in an interlabial pad without a finger insertion restriction portion as shown in FIG. 9, a ball of a finger in the top joint may be provided in a position that is not appropriate for detecting the ostium vaginae 18a. So, in some cases, it is required to perform fine adjustment of the position of the interlabial pad after detecting the ostium vaginae 18a. Further, even if a wearer detected the most appropriate position for fixing the interlabial pad, a positional displacement of finger against the interlabial pad occurs and there is a possibility that the interlabial pad can not be fixed to the position that has been detected with effort because the positional relationship between the finger and the interlabial pad is not stable. In this respect, since positional displacement of the finger against the interlabial pad according to the present invention is prevented, the interlabial pad can be fixed to the most appropriate position easily.

[Structure of the Finger Insertion Restriction Portion]

Structure of the finger insertion restriction portion provided in the interlabial pad according to the example will now be explained.

Figure 10:
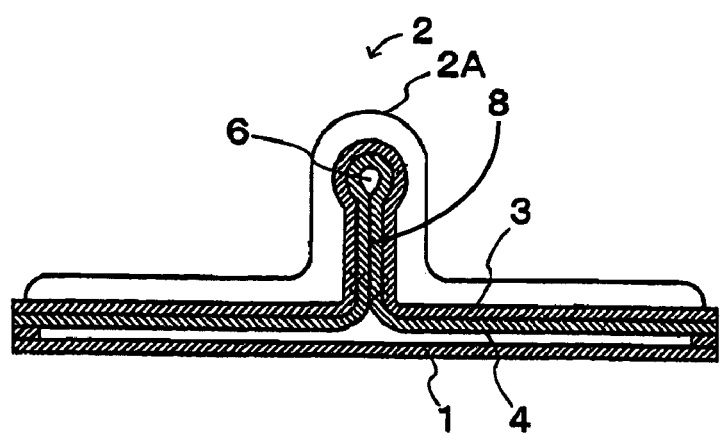
FIG. 10 is a schematic cross section diagram to explain the cross sectional structure of the finger insertion restriction portion positioned at the rear end of the interlabial pad according to the example of the present invention, showing the state only the lower regions of the sides opposite to the body of the back side sheet are bonded to each other.
Figure 11:
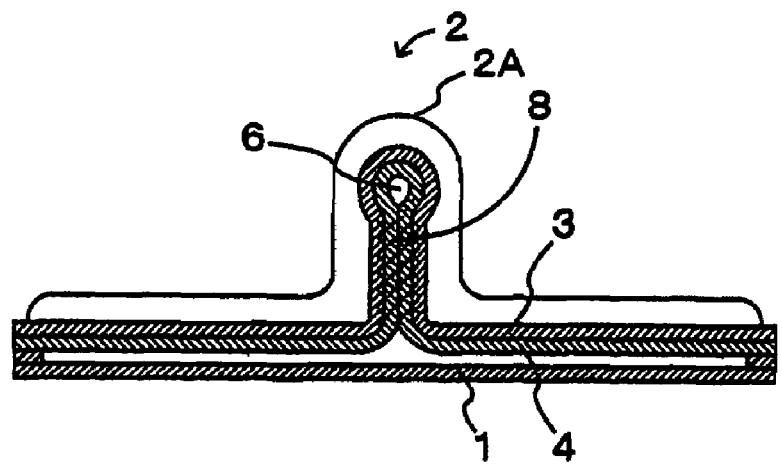
FIG. 11 is a schematic cross section diagram to explain the cross sectional structure of the finger insertion restriction portion positioned at the rear end of the interlabial pad according to the example of the present invention, showing the state that almost all regions of sides opposite to body of the back side sheet are bonded to each other.
Figure 12:
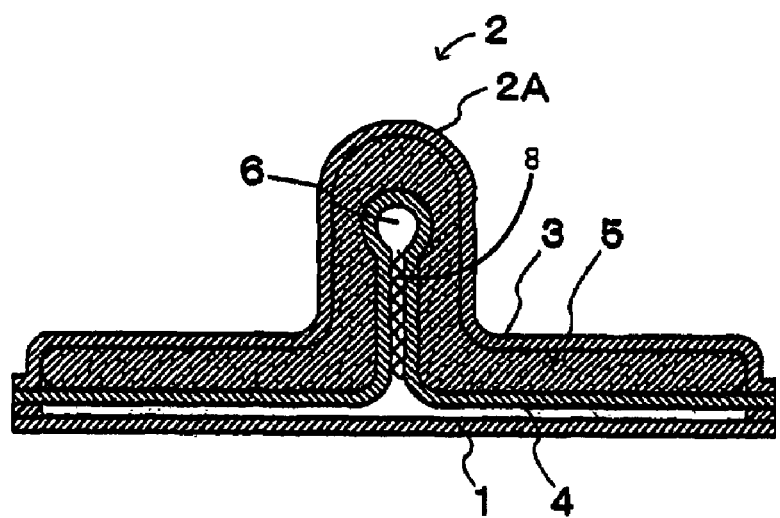
FIG. 12 is a schematic cross section diagram to explain the cross sectional structure of the finger insertion restriction portion according to the example of the present invention, showing the state that the sides opposite to body of the back side sheet are bonded with an adhesive in such a way that a space of the long convex area is crossed.

FIG. 10 is a figure of the interlabial pad according to the example seen from backward showing the state that only the lower parts of the sides opposite to body of the back side sheet are bonded to each other. FIG. 11 is a figure of the interlabial pad according to the example seen from, backward showing the state that almost all lower parts of the sides opposite to body of the back side sheet are bonded to each other. FIG. 12 is a figure showing the state that the sides opposite to body of the back side sheet are bonded to each other with adhesives, etc in such a manner that the space inside of the long convex area is crossed.

As shown above, the finger insertion restriction portion 8 is provided in the finger insertion opening 6 on the side opposite to body of the interlabial pad according to the example. The finger insertion restriction portion 8 is formed in the chevron space of the finger insertion opening 6 shown above by bonding the opposite sides to body of the back side sheet 4 to each other in the lateral direction of the interlabial pad. It stops the progress of finger insertion into the finger insertion opening 6 by narrowing the area of said space.

If the chevron space of the finger insertion opening 6 is not a "non through space", in other words, penetrated, by dint of the finger insertion restriction portion 8, a fingertip inserted from the finger insertion opening 7 may protrude from the chevron space. Further, there is a possibility that the bonding area between the back side sheet 4 and the mini sheet piece 1 may be separated or broken at the penetrated part of the finger insertion restriction portion 8. Also in this case, a fingertip may protrude from the chevron space. Thus, if a fingertip protrudes from the chevron space, some hygienic problems such as adhesion of menstrual blood to the fingertip, direct contact of the fingertip to inside of the labia may occur. Further, it becomes more difficult to fix the interlabial pad to an appropriate position by checking the position of the pubic region with a ball of a finger since positional displacement of the finger against the interlabial pad tends to take place. In order to prevent problems shown above, the finger insertion opening 6 is preferably a "non through space".

Structure of the finger insertion restriction portion 8 is formed, specifically, for example, in a part of area where sides opposite to body of the back side sheet 4 contact to each other as shown in FIG. 10 or in almost whole area where sides opposite to body of the back side sheet 4 contact to each other as shown in FIG. 11 of the marginal area (the rear end area of the interlabial pad forming a bonding area between the surface side sheet 3 and the back side sheet 4 where no absorbent body exists) situated at the rear end of the long convex area 2 of the interlabial pad, by bonding the surface side sheet 3 and the back side sheet 4 by any one of or combination of heat embossing processing, hot melt type adhesives, etc.

It is also possible to apply hot melt type adhesives in dot pattern to the overlapped area of the sides opposite to body of the back side sheet 4. Further, as shown in FIG. 12, it is also possible to apply hot melt type adhesives in a stripe pattern in the middle of the long convex area 2 (the area where the absorbent body 5 exists) in such a way that the space in the long convex area 2 is crossed. By this structure, the wear feeling is not deteriorated due to the hardening around the bonded area.

The peel strength of the bonded area of the finger insertion restriction portion 8 is preferably 100 mN/25 mm or more. A risk that a finger inserted into the finger insertion opening 6 peels and protrudes from the finger insertion restriction portion 8 can be evaded by this peel strength.

A preferable example is that the finger insertion opening 7 is provided at the position of 40% from the front end of the interlabial pad, the finger insertion restriction portion 8 is provided at the position of 90% from the front end of the interlabial pad, a hot melt type adhesive is applied in a stripe pattern with 3 mm width on the garment-facing side of the reversal side sheet 4 in such a way the long convex area is at least crossed. The dimension of the mini sheet 1 in the longitudinal direction is preferably within the range of 40 to 100% from the front end of the interlabial pad.

As shown above, the finger insertion restriction portion 8 is formed by bonding the sides opposite to body of the back side sheet 4 at the rear side of the long convex area to each other in the structure shown above. So, it is easy to form the long convex area 2 that convexes towards body around the finger insertion restriction portion 8. By bonding the opposite sides to body of the back side sheet 4 at the long convex area, the narrow width retention portion 2A to retain the shape of the section bonded and folded is formed. So, if the area from the finger insertion opening 7 to the finger insertion restriction portion 8 forming the finger insertion opening of the long convex area 2 is transformed according to the shape of a finger, the narrow width retention portion 2A retains the original width dimension at the rear of the finger insertion restriction portion 8. So, a wearer can proceed and make the long convex area stay in the vulva slit that is a particularly narrow space near the ostium vaginae using the narrow width retention portion 2A as a guiding point. By this, the position of the ostium vaginae that is positioned at the penetralia part (vestibule) is detected with a ball of a finger in the top joint in the finger insertion opening 26 and the long convex area is securely fit thereinto.

Further, since the long convex area 2 is formed by just folding the main body of the interlabial pad, it can be transformed according to the shape of the finger when fixed. A wearer can detect without sense of discomfort the position of the ostium vaginae that is positioned at the penetralia part (vestibule) with a ball of a finger in the top joint inserted into the finger insertion opening 6 through the sheet 3, 4 and the absorbent body 5 shown above. After fixing, the interlabial pad is fit to the interlabial space tightly since the long convex area 2 can be transformed according to the interlabial space.

[Mini Sheet Piece]

Figure 13:
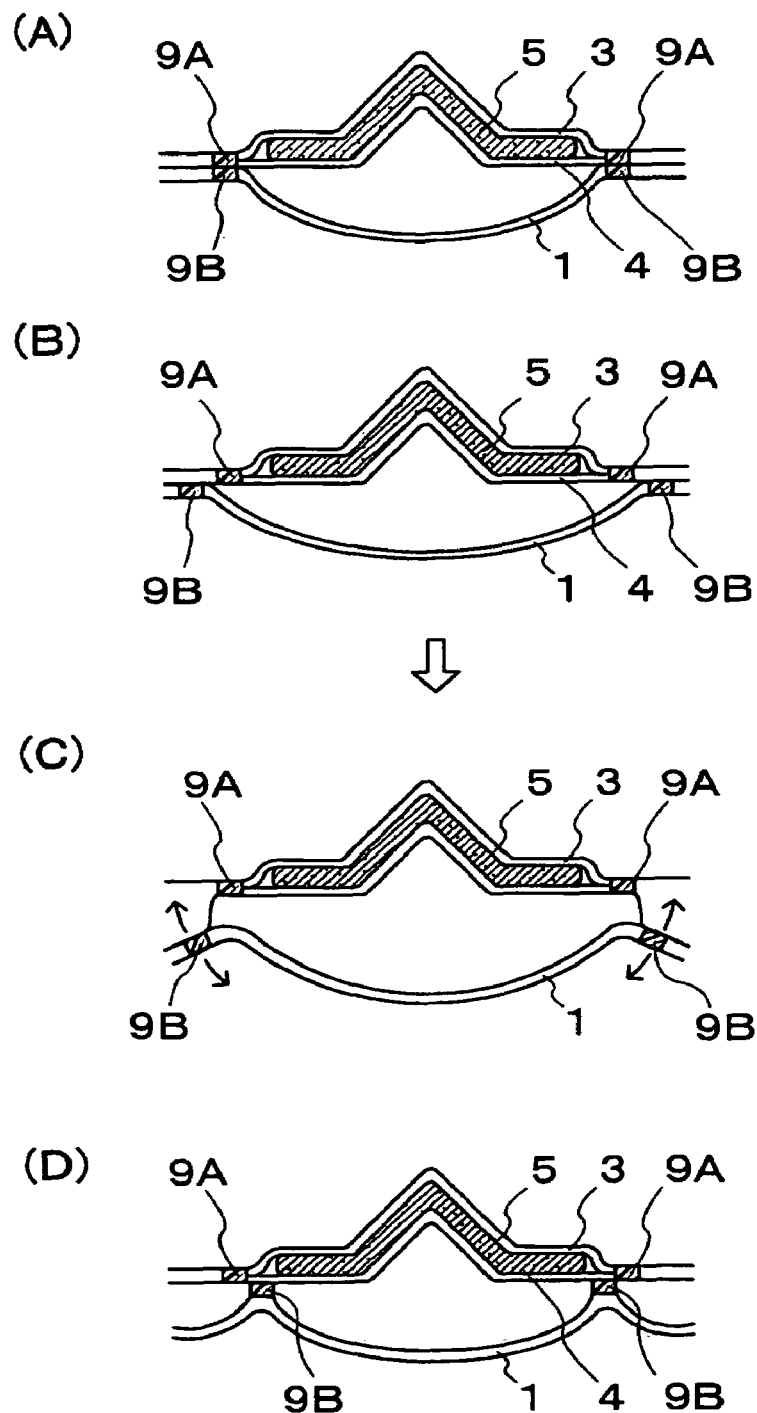
FIGS. 13A-D each illustrate a lateral cross-section of the pad to explain an embodiment of the bonded part between the mini sheet piece and the side opposite to of the back side sheet.
Figure 14:
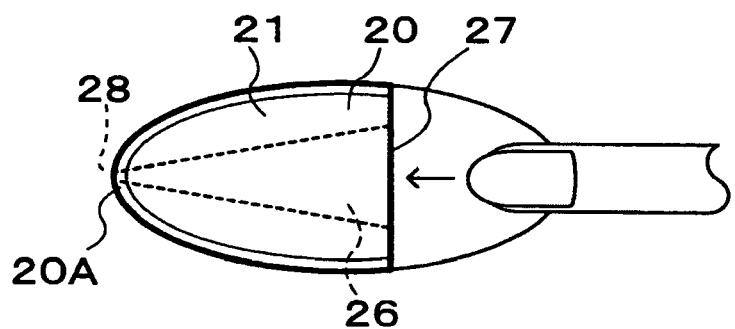
FIG. 14(A) shows the state that a finger is inserted into the interlabial pad wherein the mini sheet piece is formed to reach the end edge of the side opposite to body of the back side sheet, and the finger insertion restriction portion is formed being positioned near one end edge in the longitudinal direction of the side opposite to body.
FIG. 14(B) shows the state that a finger is inserted into the interlabial pad wherein the mini sheet piece is formed to reach a position distant by a specified dimension from the end edge of the opposite side to the body side of the back side sheet, and the finger insertion restriction portion is formed at a position to the center by a specified dimension in the longitudinal direction on the opposite side to the body side.
FIG. 14(C) is a schematic diagram to explain the state that a finger is to be inserted into the interlabial pad wherein the mini sheet pieces are separated and provided in parallel to the longitudinal direction of the opposite side to the body side.
Figure 14:
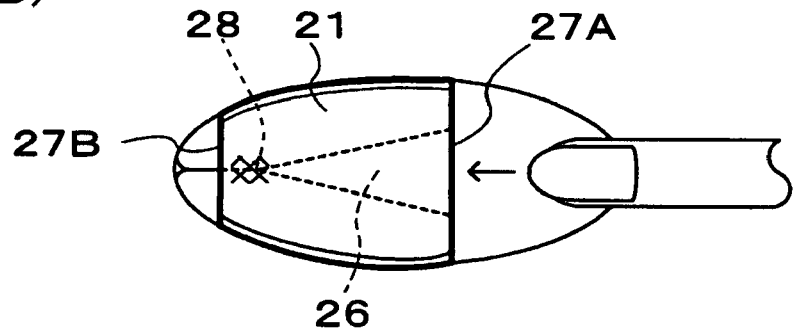
Figure 14:
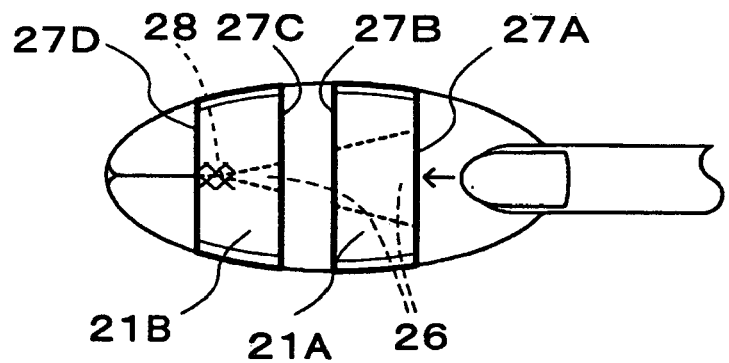

The mini sheet piece now will be explained. FIG. 13 is a lateral cross-section of the pad to explain an embodiment of the bonding part between the mini sheet piece 1 and the side opposite to body of the back side sheet 4. FIG. 14 is a figure to explain the state that mini sheet pieces 21 that are different from the mini sheet 1 in shape are attached to the side opposite to body of the interlabial pad.

[Length of the Mini Sheet Piece]

Length of the mini sheet 1 is preferably 10% or more, more preferably 50% or more to the longitudinal dimension of the interlabial pad. With this length, a finger once inserted into the finger insertion opening 6 from the finger insertion opening 7 will not be pulled out, a finger will not move in the finger insertion opening 6 and the state that a ball of a finger is facing the back side sheet 4 of the finger insertion opening 6 can be maintained.

Further, the length of the mini sheet piece 1 is preferably 80% or less, more preferably 70% or less to the longitudinal direction of the interlabial pad. "Linear dimension" of the mini sheet piece plays a role to denote "the positional relationship between the finger insertion opening 7 and the finger insertion restriction portion 8 in the longitudinal direction of the interlabial pad" and at the same time plays a role to "suggest the finger insertion direction". If the length is 80% or more to the longitudinal dimension of the interlabial pad, the mini sheet and the back side sheet are almost completely overlapped, and the function to "suggest the finger insertion direction" is not fulfilled sufficiently. As the result, a wearer may not be able to identify the finger insertion opening 7 and insert a finger thereinto. In this respect, by providing the mini sheet piece 1 having the dimension shown above, the problems can be evaded, and quick and smooth wearing of the interlabial pad on a fingertip is secured.

[Bonding Position of the Mini Sheet Piece in the Lateral Direction]

In the interlabial pad according to the present invention, the bonding area 9A between the surface side sheet 3 and the back side sheet 4 forms the side edge of the interlabial pad in the lateral direction. As shown in FIG. 13(A), if the bonding area 9B of the mini sheet piece 1 and the back side sheet 4 is positioned and fixed to this side edge area, the side edge of the interlabial pad becomes hardened, which may cause deterioration of wearing feeling.

This problem can be evaded by providing a bonding area other than the side edge shown above to fix the mini sheet piece 1. In this case, for example, as shown in FIG. 13(B), if the bonding area 9B between the mini sheet piece 1 and back side sheet 4 is positioned outside of the bonding area 9A, as shown FIG. 13(C), the bonding area 9B is likely to apart from the back side sheet 4 according to the action of a wearer, generating friction to skin to apply stimulus to a wearer. So, as shown in FIG. 13(D), the positions of bonding area 9A and 9B is preferably displaced, and the bonding area 9B is preferably provided in the position nearer to the center in the lateral direction of the interlabial pad than the bonding area 9A.

It is possible to use pressure-sensitive hot melts, thermosensitive hot melts, etc. for the adhesive to fix the mini sheet 1. It is possible to adopt sheet pattern, linear pattern, spiral pattern, dot pattern, etc for application of the adhesive. The mini sheet piece 1 may be cut in advance to conform to the fixing position shown above. The cutting process may be performed at the same time as other sheets with only the bonding position being different from other sheets. <Non-bonding area of the mini sheet piece in the lateral direction of the interlabial pad>

The relationship between the shape of the mini sheet piece and the finger insertion restriction portion will now be explained. As shown in FIG. 14(A), if the mini sheet piece 21 forms the same shape as a part of the interlabial pad 20 and fixed in such a manner that it does not have non-bonding areas except the finger insertion opening 27, it is possible to provide the finger insertion restriction portion 28 at the rear end 20A of the interlabial pad 20. On the other hand, as shown in FIG. 14(B), if the mini sheet piece 21 is fixed in such a way that the second non-bonding area 27B exists in addition to the first non-bonding area 27A forming the finger insertion opening with the side opposite to the interlabial pad 20, the second non-bonding area 27B is provided in the rear of the finger inserting restriction portion 28. By this the mini sheet piece 21 is provided in such a way that outside of a fingertip (nail side) is covered and a fingertip (nail side) is guided to the finger insertion restriction portion 28 securely resulting in reducing troubles that the ostium vaginae is not easily detected because a ball of a finger in the top joint is removed from the side opposite to body in the finger insertion opening 6. Further, since the bonding area between the interlabial pad 20 and the mini sheet piece 21 can be reduced, the area hardened by bonding them is reduced to improve wearing feeling.

Multiple mini sheet pieces may be fixed. In this case, as shown in FIG. 14 (C), the non-bonding areas of the mini sheet piece 21A and 21B in the lateral direction of the interlabial pad 20 is pluralized such as 27A, 27B, 27C, 27D. The finger insertion restriction portion 28 should be provided in front of the non-bonding area 27D at the backmost side of the interlabial pad 20, which is the end edge of the non-bonding area 27A and the finger inserting direction. By this, a fingertip can be guided into the finger insertion restriction portion 28 to prevent a ball of a finger in the top joint from removing from the finger insertion opening 26. In addition to that, since the mini sheet piece 21B is positioned wrapping a fingertip, exposure of the fingertip can be prevented. In addition to that, the area where a finger is covered by the mini sheet 21A and 21B can be reduced resulting in enlargement of flexibility in finger movement such as bend, stretch of a finger, enabling a finger to move more naturally in the operation that the interlabial pad 20 is pinched between the labia to further reduce positional displacement of the interlabial pad 20 against the labia. Multiple mini sheet pieces may be different in shape from one another. Mini sheet 21A and 21B may be different in shape to each other as shown in the example.

[Nail Tip Escapement]

The nail tip escapement provided in the finger insertion opening will now be explained.

Figure 15:
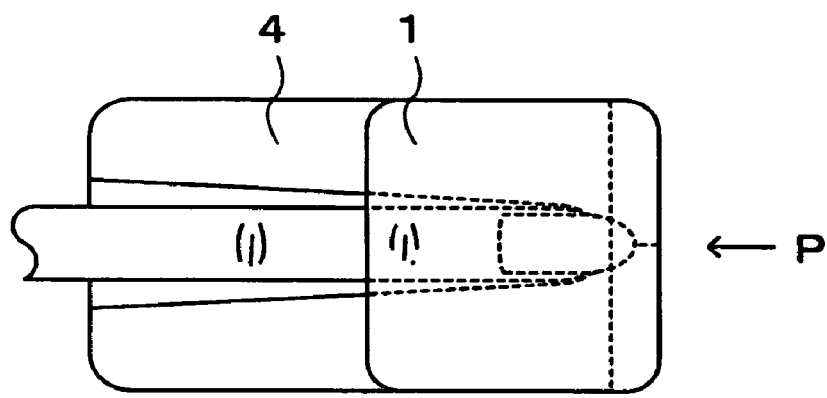
FIG. 15 is a schematic plane view showing the state of a finger with dotted lines inserted into the finger insertion opening using the interlabial pad where the nail tip escapement is formed at the finger insertion restriction portion.
Figure 16:
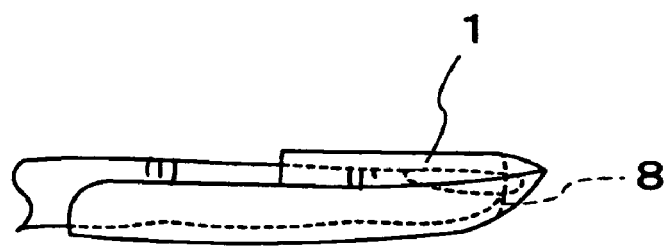
FIG. 16 is a schematic side view showing the state of a finger with dotted lines inserted into the finger insertion opening using the interlabial pad where a nail tip escapement is formed at the finger insertion restriction portion.
Figure 17:
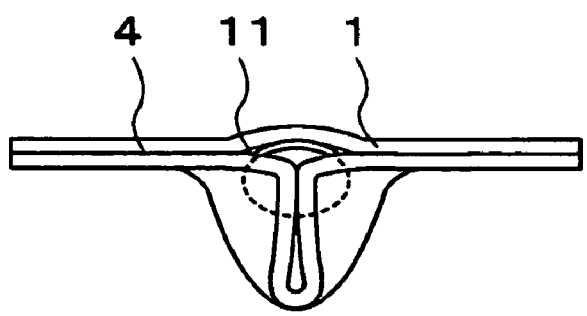
FIG. 17 is a schematic end elevation showing the state of a finger with dotted lines inserted into the finger insertion opening using the interlabial pad where the nail tip escapement from which a nail tip protrudes is formed at the finger insertion restriction portion.

FIG. 15 is a schematic plan view showing in broken lines the state of a finger inserted into the finger insertion opening of the interlabial pad where a nail tip escapement is formed at the finger insertion restriction portion. FIG. 16 is a schematic side view showing the state of a finger inserted into the finger insertion opening of the interlabial pad where a nail tip escapement is formed at the finger insertion restriction portion. FIG. 17 is a schematic end elevation of FIG. 15 seen from the sagittal direction P.

The interlabial pad according to the present invention, as shown in FIG. 15, nail tip escapement 11 can be provided at the finger insertion restriction portion 8 in such a way that a nail tip of a finger can protrude from the same.

With this structure, as shown in FIG. 16, only a nail tip can be protruded from the nail tip escapement 11 with the finger staying at the position where the finger insertion restriction portion 8 exists. By this, as shown in FIG. 17, even a wearer with longer nails can retain the interlabial pad at the fingertip by protruding only a nail tip from the nail tip escapement 11 in such a state that a ball of a finger in the top joint contacts the back side sheet 4 at the vicinity of the finger insertion restriction portion 8 that is the most appropriate for detecting the ostium vaginae.

In addition, since the finger insertion restriction portion 8 is formed at the position displaced from one end edge towards the center along the longitudinal direction on the opposite side to the body side, the back side sheet 4 exists for the nail tip protruded from the nail tip escapement 11 preventing adhesion of menstrual blood to the nail tip to improve sanitary conditions.

[Dimension of Finger Insertion Opening]

Figure 18:
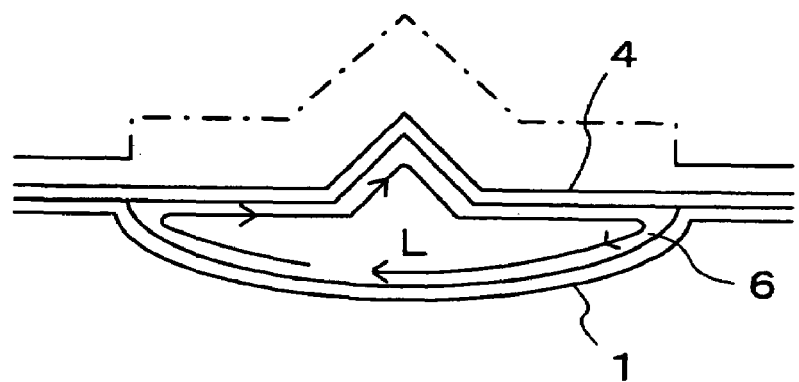
FIG. 18 is a schematic diagram to explain the length of total inside perimeter of the finger insertion opening of the interlabial pad according to the example of the present invention.

Dimension of the finger insertion opening will now be explained. FIG. 18 is a schematic view to explain the total inside perimeter of the finger insertion opening 7 of the interlabial pad according to the example.

In FIG. 18, the sections not required for explaining the inside perimeter of the finger insertion opening 7 are denoted in dashed lines, wherein the inside perimeter of the finger insertion opening 7 is the distance shown by L.

The total inside perimeter of the inside of the finger insertion opening 7 shown by "L" in FIG. 18 is preferably 30 to 120 mm and more preferably 40 to 80 mm. If the total inside perimeter length of the finger insertion opening 7 is smaller than 30 mm, the finger insertion opening 7 itself gets smaller to make insertion and pulling out of a finger difficult. If it is larger than 120 mm, it becomes hard to make a ball of a finger securely in touch with the back side sheet 4 in the finger insertion opening 6 resulting in poor retention of the interlabial pad by a finger to cause troubles in fixing the interlabial pad.

[Dimension of the Interlabial Pad]

Figure 19:
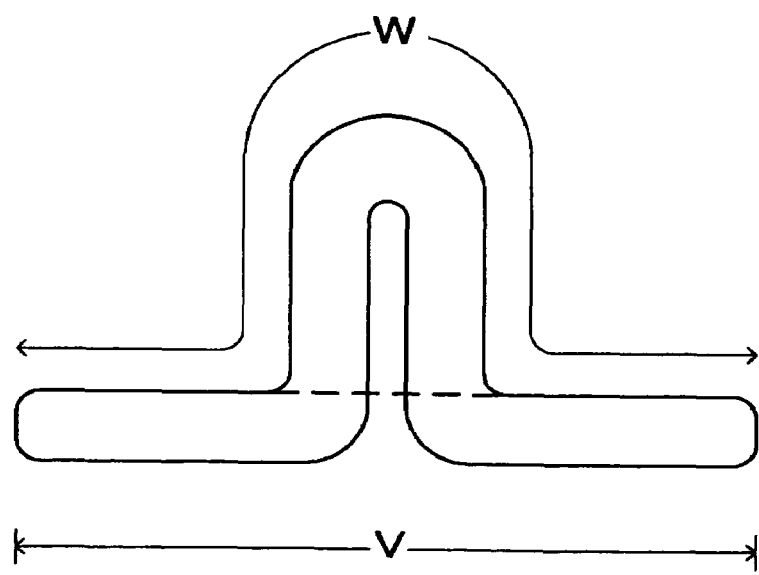
FIG. 19 is a schematic diagram to explain the linear dimension in the lateral direction of the interlabial pad.

The apparent dimension of the interlabial pad will now be explained. FIG. 19 is a figure to explain the linear dimension of the interlabial pad in the lateral direction.

The longitudinal direction of the interlabial pad is preferably 50 to 160 mm, more preferably 80 to 130 mm. With regard to this, if the linear dimension of the longitudinal direction is longer than 160 mm, the friction generated between the area that is not pinched by the interlabial space and shorts or sanitary napkins may exceed the pinching force by both labia resulting in removal of the interlabial pad. In the meantime, if the linear dimension in the longitudinal direction is less than 50 mm, since the area to be pinched by the labia becomes smaller, the contact area between the labia and the interlabial pad decreases to cause removal of the interlabial pad.

Apparent linear dimension of the interlabial pad in the lateral direction is preferably 10 to 60 mm, more preferably 20 to 40 mm. If the linear dimension in the lateral direction is longer than 60 mm, the area not pinched by the labia is rubbed by thighs of a wearer and the generated friction exceeds the pinching force by both labia resulting in removal of the interlabial pad. In the mean time, if the linear dimension of the lateral direction is shorter than 10 mm, since the area to be pinched between the labia becomes smaller, the contact area between the inside of the labia and the interlabial pad decreases to cause higher risk in removal of the interlabial pad.

"Apparent" used above denotes the distance between two points with the shortest linear dimension (falls under V in FIG. 19). This is a deliberate definition considering the case where the distance between two points in plan extended from a three dimensional shape is sometimes used as an actual distance (falls under W in FIG. 19) in relation to manufacturing process.

[Transformation Example of the Interlabial Pad]

Other examples of the interlabial pad according to the present invention will now be explained.

Figure 20:
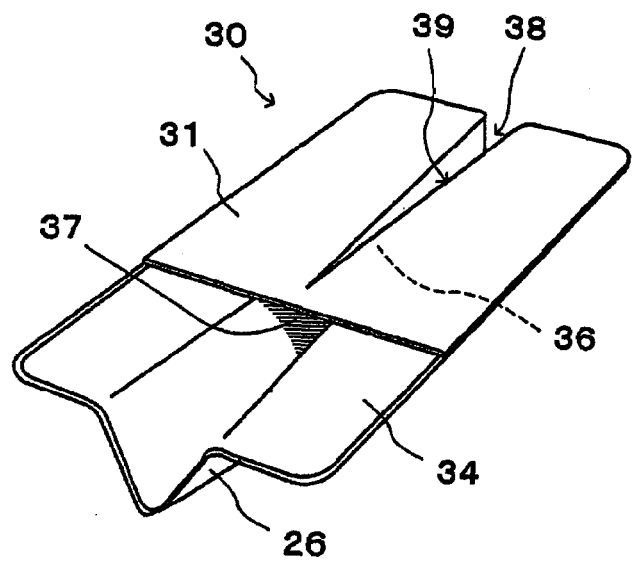
FIG. 20 is a schematic perspective view showing a transformational example of the interlabial pad according to the the present example and the structure where the finger insertion direction restriction portion is formed with the shape of the mini sheet piece folded into the finger insertion opening.
Figure 21:
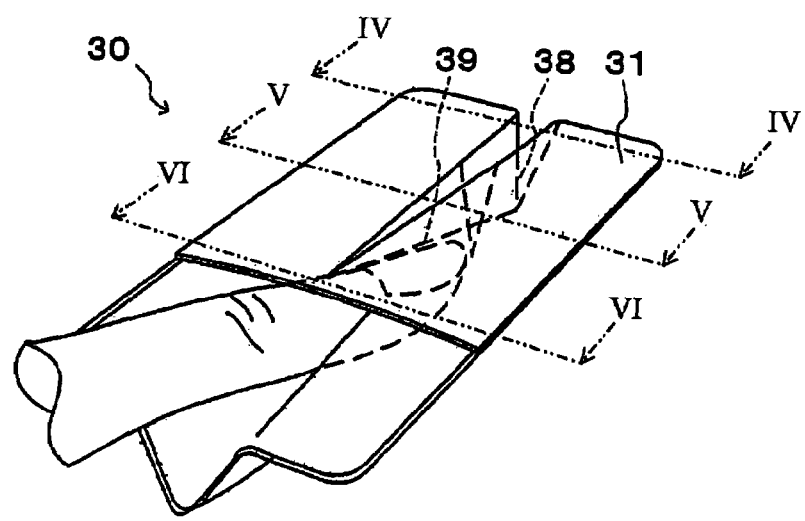
FIG. 21 is a schematic diagram showing an example of the transformed interlabial pad according to the example of the present invention and the state that the inserting direction of a finger is forced to slant towards the opposite side to the body side facing the finger insertion restriction portion.
Figure 22:
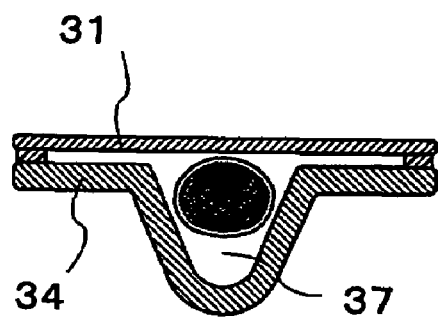
FIG. 22 is a cross section diagram of a cross section VI-VI of the interlabial pad in FIG. 21 showing the state of a finger in the finger insertion opening.
Figure 23:
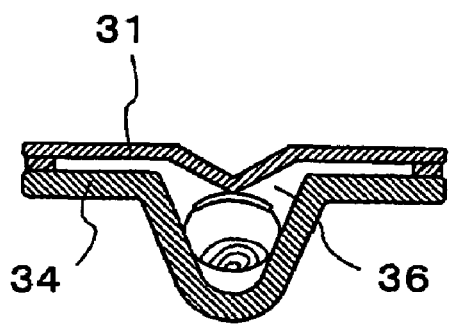
FIG. 23 is a cross section diagram of a cross section V-V of the interlabial pad in FIG. 21 showing the state of a finger in the finger insertion opening.
Figure 24:
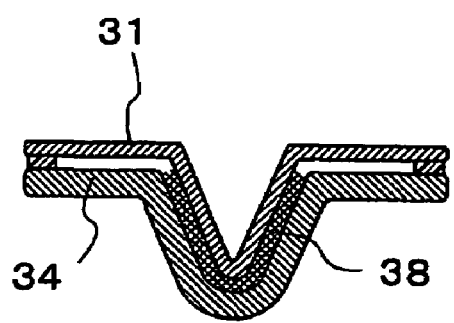
FIG. 24 is a cross section diagram of a cross section IV-IV of the interlabial pad in FIG. 21 showing the finger insertion restriction portion.

FIG. 20 is a schematic perspective figure showing the structure where the finger insertion direction restriction portion 39 is formed by dint of the shape of the mini sheet piece 31 folded into the finger insertion opening 36. FIG. 21 is a schematic diagram explaining the state that a finger is inserted into the interlabial pad 30 where the finger insertion restriction portion 39 is formed. FIG. 22 is a diagram of a cross section VI-VI of FIG. 21. FIG. 23 is a diagram of a cross section V-V of FIG. 21. FIG. 24 is a diagram of a cross section IV-IV of FIG. 21.

In the interlabial pad 30 according to the example, as shown in FIG. 20, the finger insertion direction forcing portion 39 is formed to force the insertion direction of a finger in the finger insertion opening 36 to be slanted towards the opposite side of body of the back side sheet 34 facing the finger insertion restriction portion 38.

With this structure, insertion direction of a finger is forced to slant towards the finger insertion restriction portion 38 by dint of the finger insertion direction forcing portion 39 in the process of inserting the finger proceeded from the finger insertion opening 37 into the finger insertion opening 36. So, it is possible to make a ball of a finger in the top joint securely come into contact with the opposite side to the body side of the back side sheet 34 when the finger reached the finger insertion restriction portion 38.

In addition to that, in the interlabial pad 30 according to the example, as shown in FIG. 21, the finger insertion direction forcing portion 39 is formed by folding mini sheet piece 31 into the finger insertion opening 36 in such a way that the distant dimension between the mini-sheet piece 31 and the back side sheet 34 decreases gradually. By this, a finger inserted into the finger insertion opening 36 is inserted obliquely downward towards the finger insertion restriction portion 38 by the folding shape. Since the finger insertion restriction portion 38 is at least formed by bonding both sides of the finger insertion opening 36 in the lateral direction on the opposite side to the body side of the back side sheet 34, a finger is positioned with a clearance between the mini sheet piece 31 and the back side sheet 34 near the finger insertion opening 37. And the distance dimension between the mini sheet piece 31 and the back side sheet 34 decreases and a finger in the finger insertion opening 36 is retained from above and beneath since the mini sheet piece 31 is folded gradually, as shown in FIG. 23, on the way to the finger insertion restriction portion 38. Further, as shown in FIG. 24, near the finger insertion restriction portion 38, it is impossible to insert a finger between the back side sheet 34 and the mini sheet piece 31 and proceed of finger insertion is prohibited completely.

[Construction Materials of the Interlabial Pad]

<Water Permeable Sheet>

Materials that are liquid hydrophilic and do not apply stimulus to skin are used for water permeable sheets provided at the body-facing side of the interlabial pad. They include nonwoven fabrics used alone or in combination manufactured by methods such as melt blown, spun bond, point bond, through air, needle punch, wet spun lace, foam film.

A fibrous sheet may be either a single fiber or a complex fiber made into a sheet made from either alone or in combination forming a core sheath structure of rayon, acetate, cotton, pulp or synthetic resins.

Among these materials, considering liquid mobility from inside of the labia, chemical stimulation due to activators and the adhesiveness to inside of the labia, a spun lace nonwoven cloth wherein rayon of fineness 1.1 to 4.4 dtex and fiber length 7 to 51 mm is laminated by 40 to 80% of total specific weight per unit area on the body-facing side, rayon of fineness 1.1 to 4.4 dtex, fiber length 7 to 51 mm, 14 to 42% of total specific weight per unit area and PET of fineness 1.1 to 4.4 dtex, fiber length 7 to 51 mm, 6 to 18% of total specific weight per unit area are mixed to be laminated in such a way total specific weight per unit area of two layers is 20 to 60 $g/m^2$ on the garment-facing side, then, fibers are spun with one another by water flow spun lace and dried, the thickness thereof is adjusted in the range from 0.13 to 0.50 mm is preferable. In this case, bulkiness will be maintained even if the water permeable sheet is in wet condition by mixing PET on the garment-facing side to keep the adhesion to the inner wall of the labia.

<Absorbent Body>

Materials to be used for the absorbent body contained in the interlabial pad include pulp, chemical pulp, rayon, acetate, natural cotton, water-absorbent polymer, fibrous water-absorbent polymer, synthetic fiber. They may be used alone or as a mixture of two or more. A mixture blended as required is made into a sheet by technologies such as pressure bonding by embossing, lacing by needling well known in the art. The sheets may be adjusted by bulkiness adjustment, layering, folding, etc as required.

Materials for a sheet may be used in a sheet shape or may be used by processing the same into powder. Their usages are not limited.

It is preferable for the absorbent body, although any material can be used as long as it is capable of absorbing and holding liquid (body fluid), to be bulky, hard-to-be deformed, less chemically stimulant, and highly flexible to fit into the labia. Specifically, a nonwoven sheet in which, 50 to 150 $g/m^2$ of pulp selected from the range of the fiber length of 1 to 10 mm is laminated on the garment face side and, on the body face side, 150 to 250 $g/m^2$ of a mixture obtained by mixing 60 to 90% of rayon with 1.1 to 4.4 dtex fineness and 20 to 51 mm fiber length with 40 to 10% of natural cotton is laminated, which then to be formed into a sheet by dotted embossing to have 2 to 10 mm bulkiness, and more preferable to have 3 to 5 mm bulkiness. Thereby, liquid can be easily transmitted from the body face side to the garment face side resulting in the improvement of the absorbing and holding capacity. Furthermore, by providing a mesh spun lace nonwoven fabric of rayon with 1.1 to 4.4 dtex fineness and 25 to 51 mm fiber length by a specific weight per unit area of 15 to 40 $g/m^2$, the liquid transmitted from the body face side can be dispersed by the mesh spun lace to be induced to almost all over the region of the pulp layer. Therefore, more liquid can be effectively absorbed.

<Water Impermeable Sheet>

Materials that can prevent menstrual blood retained in an absorbent body from getting out of the interlabial pad can be used for water impermeable sheets. If they are moisture permeable, it is possible to reduce humidity and unpleasantness during wearing the interlabial pad.

Such materials include, for example, a sheet film wherein a synthetic resin is transformed into a membrane, an air permeable film made by filling an inorganic filler and performing pulling process, a laminated material wherein a paper, an unwoven cloth and a film are combined, an air permeable liquid shutoff sheet having capillaries arranged towards absorbent body with capillaries hole area rate 10 to 30% and hole diameter 0.1 to 0.6 mm.

Further, when considering flexibility not spoiling wearing feeling, for example, a film selected from the range of specific weight per unit area from 15 to 30 $g/m^2$ composed mainly of low density polyethylene (LDPE) resin with density of 0.900 to 0.925 $g/cm^3$ is preferably used. More preferably, said film is emboss processed to reduce contact ratio and friction resistance by providing convex bossing in order to reduce a risk that the interlabial pad falls off from the labia due to a large friction caused by contact with other non-permeable sheets, pads used at the same time, underwear, etc when the interlabial pad is fixed to the interlabial space.

<Mini Sheet Piece>

Materials that are the same as said water permeable sheets or the water impermeable sheets may be used for the mini sheet piece. Materials with extensity or elasticity at least in the lateral direction are preferably used.

By using such materials for the mini sheet piece, even if the size of a fingertip of a wearer is larger than the specified finger insertion opening, the interlabial pad according to the present invention can be used effectively irrespective of the fingertip size of a wearer because the mini sheet piece at least stretch in width direction.

Basically, materials with elasticity include: for example, synthetic rubbers such as styrene-butadiene-styrene block copolymers (SBS), styrene-isoprene-styrene block copolymers (SIS), urethane; films made from amorphous olefin resins with density selected from 0.88 to 0.900 $g/cm^3$, porous foam films, nets. A nonwoven cloth and a cloth wherein a fiber spinning filament made from a synthetic rubber is woven into an woven cloth can be also used. Further, a spun bond nonwoven cloth and a melt-blown nonwoven cloth composed mainly of a synthetic rubber and a foamed sheet can be used.

Considering flexible feeling when wearing, a porous foam film made from styrene-ethylene-butadiene-styrene block copolymer (SEBS) adjusted in the range of thickness from 15 to 40μ, hole area from 0.28 to 1.77 $mm^2$, hole area rate from 40 to 70% is preferably used.

Nonwoven fabrics include: spun lace nonwoven fabrics made from complex synthetic fibers such as PE/PP, PE/PET, PP/PP having thermal shrinkage property, wherein core component has a high melting point and the sheath component has a lower melting point, and fibers are laced by water pressure; shrink type nonwoven fabrics wherein shrinkage of fibers are accelerated by performing re-hot air processing; so called extensible spun bonds wherein continuous long fibers are applied with tentering after they are made into a sheet by heat seal.

More specifically, preferable materials rich in flexiblity and drape feeling include shrink type nonwoven fabrics made from compound synthetic fiber such as PE/PP, PE/PET, PP/PP with fineness in the range from 1.1 to 4.4 dtex and the length in the range from 7 to 51 mm, having thermal shrinkage property, wherein the core component has a high melting point and sheath component has a lower melting point, a specific weight per unit area is adjusted in the range from 10 to 60 g/m². Further, laminated types of said materials can be also used. Materials without extensity applied with extensity before use included: among nonwoven fabrics, through air nonwoven fabrics made from complex synthetic fibers such as PE/PP, PE/PET, PP/PP having thermal shrinkage property, wherein core component has a high melting point and the sheath component has a lower melting point; spun lace nonwoven fabrics wherein fibers are entangled by water pressure; spun bond nonwoven fabrics transformed into a sheet by layering continuous fibers; needle punch nonwoven fabrics wherein fibers are entangled to one another by needles; SMS nonwoven fabrics wherein spun bond and melt-blown are layered in multiple layers to form a sheet; porous foam films; films mainly composed of PE resins. They may be used either alone or in combination of two or more.

Further, said materials can be applied with extensity by corrugate processing wherein materials are fit between male and female dies and a shape is embossed by heat, temperature and pressure. More specifically, through air nonwoven fabrics composed mainly of complex synthetic fibers adjusted to the range of fineness 1.1 to 4.4 dtex and a specific weight per unit area of 10 to 60 g/m², corrugated so that they can extend in the lateral direction are preferred. Corrugate processing is performed in such a way that male and female dies are provided so that extensity is preferably obtained in the range of at least 10% and, more preferably, 20 to 50%, still further preferably, have a behavior in the range of 0.01 to 0.05N/25 mm of loads when 30% extended (test condition: Tensilon tensile tester, speed, 100 mm/min, chuck interval, 100 mm). Other methods to apply extensity include cut lines, circular cutouts.

<Adhesives>

Hot melt type adhesives generally used can be used for joining (bonding) materials. Examples include pressure sensitive hot melt adhesives and heat sensitive hot melt adhesives. Pressure sensitive hot melt adhesives are obtained by melting and mixing adhesiveness granting agents such as terpene resins, rosin resins and plasticizers such as waxes with synthetic rubber resins as main components including SIS, SBS, styrene-ethylene-butadiene-styrene block copolymers (SEBS), styrene-ethylene-propylene-styrene block copolymers (SEPS). Examples of heat sensitive hot melt adhesives include the ones composed mainly of olefin resins such as poly-a-olefin as a base resin. As shown above, there are many types of adhesives. Considering stability of application, however, it is desirable to use heat sensitive hot melt adhesives. Heat sensitive hot melt adhesives with higher application stability are those contain 45 to 55% of poly-a-olefin by weight, 10 to 15% of a plasticizer by weight and 35 to 45% of an adhesiveness granting agent by weight that are melt and blended. 0.1 to 1.0% of antioxidants, fluorescence inhibitors by weight may be added to this type of heat sensitive hot melt adhesives.

[Configuration of the Interlabial Pad Applied with Biodegradability, Water Dispersibility and Water Solubility]

The interlabial pad according to the present invention is preferably composed of biodegradable materials and/or water dispersible materials and/or water soluble materials. These kinds of interlabial pads can be fallen off into lavatory bowls as they are after use. So, pads can be disposed easily and cleanly. In addition, wastes in bathrooms can be reduced.

In this Specification, "biodegradability" means that a substance is decomposed into gas such as carbon dioxide or methane, water, and biomass under anaerobic or aerobic condition according to the natural process under the existence of bacteria represented by actinomycetes and other microbes, and also means that the biodegradability (biodegradable rate and biodegradable degree) of the substance equals to a material naturally generated such as fallen leaves or a synthetic polymer generally recognized having the same biodegradability under the same environment. "Water dispersibility" has the same meaning as water degradability. It means a characteristic in which, while having no influence when used in a limited amount of moisture (menstrual blood), in a large amount of water or water current, the fabric is easily dispersed into small pieces at least to a degree where an ordinal toilet plumbing is not clogged. "Water solubility" is a characteristic in which, while having no influence when used in a limited amount of moisture (menstrual blood), the fabric is soluble in a large amount of water or water current.

<Water Permeable Sheet>

Materials that can be used for water permeable sheets include: wet forming spun lace nonwoven fabrics with fiber length selected from 1 to 15 mm. Other materials include hydrolyzed biodegradable resins such as polylactic acid, polybutylene succinate. Examples include melt-blown nonwoven fabrics made from polylactic acid, whose specific weight per unit area is adjusted to the range of 20 to 60 g/m² and spun bond nonwoven fabrics whose specific weight per unit area is adjusted to the range of 15 to 30 g/m² and fineness is adjusted to the range of 1.1 to 3.3 dtex. Materials for nonwoven fabrics may or may not be holed.

For other materials, an acetate, a single synthetic fiber and a tow that is a continuous fiber composed of laminated bodies may be used by adjusting them to the range of specific weight per unit area from 50 to 300 g/m² and fibrillating their fibers.

<Absorbent Body>

Nonwoven cloth sheets obtained by needling can be used for absorbent bodies. It is desirable to use carboxymethyl cellulose fibers considering biodegradability of super absorbent polymer materials.

<Water Impermeable Sheet>

Materials usable for water impermeable sheets include: PVA film; film sheets where one or both sides of, or partial surface of PVA film is applied with water-repellent by applying silicone, etc; PVA film mixed with silicone; starch films; films made from biodegradable resins of hydrolyzed polylactic acid; polybutylene succinates, etc and laminated papers with tissues, etc. If required, 0.1 to 5% of inorganic pigments may be mixed to color.

It is desirable to use laminated papers where films made from polylactic acid are laminated with tissues selected from the range of thickness of 10 to 20μ and specific weight per unit area of 15 to 20 g/m² and further composite area ratio when laminated is 5 to 40% considering maintenance of leakage resistance under hyper humidity and lower loads to septic tanks.

<Mini Sheet Piece>

Materials usable for the mini sheet piece include: films, spun bond nonwoven fabrics, melt-blown nonwoven fabrics, etc made from biodegradable materials such as polylactic acid; polybutylene succinate; films and nonwoven fabrics, etc made from soluble materials such as PVA, CMC; water dispersible tissues, spun lace nonwoven fabrics, etc composed mainly of cellulose fibers, recycled cellulose fibers, etc.

Of these, spun bond nonwoven fabrics or melt-blown nonwoven fabrics composed mainly of biodegradable materials that are made into sheets whose fineness is adjusted to the range from 0.1 to 3.3 dtex, specific weight per unit area is adjusted to the range of 15 to 40 g/m$^2$, obtained from said mechanical corrugate processing are preferred.

<Bonding Methods>

Bonding methods include: bonding with polyvinyl alcohol, etc with water solubility or water swellingness, heat seal, hydrogen bonding, etc. They are used alone or two or more of them are used at the same time.

It is possible to make a pad contact the interlabial space or external genitals by forming adhesion on a part of the body-facing side of the surface side sheet. It is also possible to prevent gaps from being generated between the pad and the body even when postures of a wearer are changed suddenly. So, a wearer can act freely without anxiety and restraining her activities.

It is possible to form an adhesive area by applying adhesives on the surface side sheet. Adhesives usable in the present invention include: water-soluble polymers, crosslinking agents, plasticizers, gel adhesives composed of water, etc. More specifically, examples of water soluble polymers include: gelatin, sodium polyacrylic acid, polyvinyl alcohol, carboxymethyl cellulose, etc. Examples of crosslinking agents include water-soluble metal salts such as calcium chloride, magnesium sulfate. Examples of plasticizers include: glycerin, wax, paraffin, etc.

Besides them, it is possible to use pressure sensitive hot melts to form adhesive areas. Pressure sensitive hot melts are obtained by melting and blending adhesiveness granting agents such as terpene resins, rosin resins; and plasticizers such as waxes with synthetic rubber resins such as SIS, SBS, SEBS, SEPS as a main component. Further, it is also possible to use silicone resin adhesives. Example of silicone resin adhesives include mixtures composed mainly of silicone resins and fluorocarbon resins, mixed with crosslinking agents such as platinum, molybdenum, antimony, and also mixed with plasticizers such as esters waxes, glycerin, machine oils.

As shown above, there are varied types of adhesives to form adhesive areas. However, if stability of application is considered, pressure sensitive hot melts are preferred. Examples of pressure sensitive hot melt adhesives with higher application stability are the ones where 15 to 25% of SEBS, 15 to 35% of a plasticizer by weight, 40 to 70% of an adhesiveness granting agent by weight are melted and blended. 0.1 to 1.0% of antioxidants, fluorescence inhibitors by weight may be added to this kind of pressure sensitive hot melt adhesives.

It is desirable to coat adhesive areas with a sheet of a tissue paper that is a separate paper generally available or a sheet of a film coated with a silicone resin. This can prevent adhesives from defeaturing and removing during storage.

Figure 25:
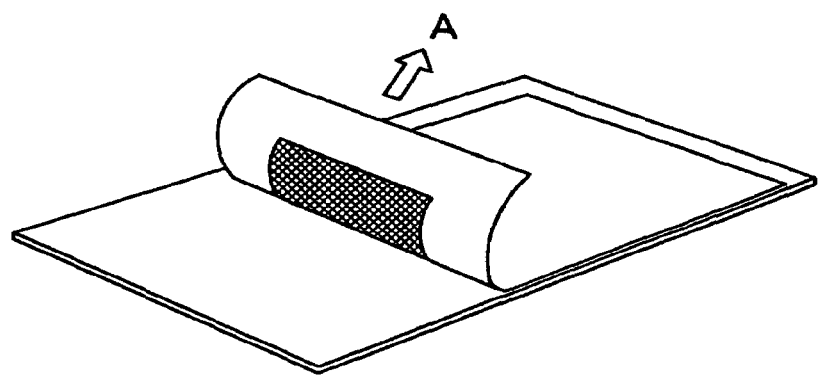
FIG. 25 is a schematic view to explain a method to measure the peel strength of adhesives for evaluating the adhesive force thereof.
Figure 26:
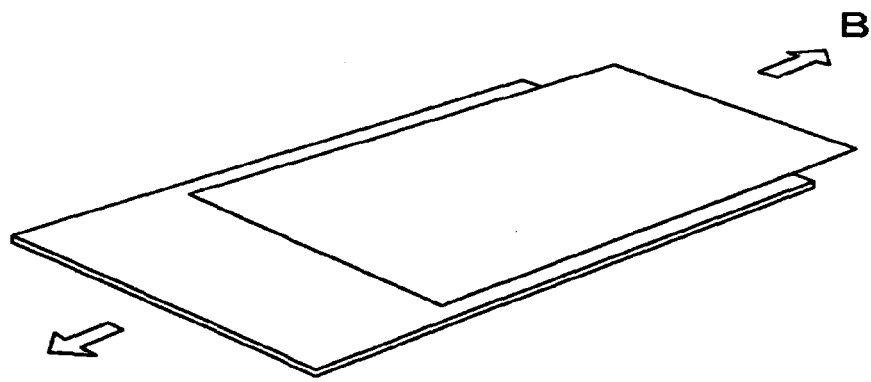
FIG. 26 is a diagram to explain a method to measure the shearing strength of adhesives in a valuation method of the adhesive strength of the adhesive formed on the body side surface of the surface side sheet.

Adhesives may be placed in plane, dot pattern, grid pattern, stripe pattern, etc. Application positions of adhesives are not particularly limited so far as they make fixing on body possible. It is particularly desirable to apply in stripe pattern of about 1 to 5 mm width near the both sides of the surface side sheet considering pubic hairs at the near side of the labia. An example of evaluating methods for the adhesive force will now be explained. These evaluation methods are to measure peel strength (refer to FIG. 25) and shear strength (refer to FIG. 26) of adhesives using a constant speed stretch tensile testing machine and stainless steel boards of 80 mm×50 mm (length×width). Before starting an evaluation test, an adhesive is applied by 25 mm×50 mm (width×length) on a polyethylene film that has almost same size as the stainless board. The film is let stand for 30 minutes under room temperature (20° C.). Then, the polyethylene film is gently put on the stainless board so that the adhesive contact the board. A roller with weight of 2 kg is applied by just one-way. After that, test strips are made by letting it stand under room temperature (20° C.) for 30 minutes. In the peel-strength test, the polyethylene film of the test strip is peeled by pulling it toward a direction indicated by an arrow A in FIG. 25. In the shear strength test, the film is pulled toward a direction indicated by an arrow B in FIG. 26. With regard to the test conditions, chuck interval (clamping interval) is 70 mm and pulling speed is 100 mm/min. In this test, the measured value of the peel strength is preferably 100 to 200 mN/25 mm, shear strength is preferably 2900 to 15000 mN/25 mm. These values are decided considering loads to skin of a wearer.

[Wrapping Body]

Figure 27:
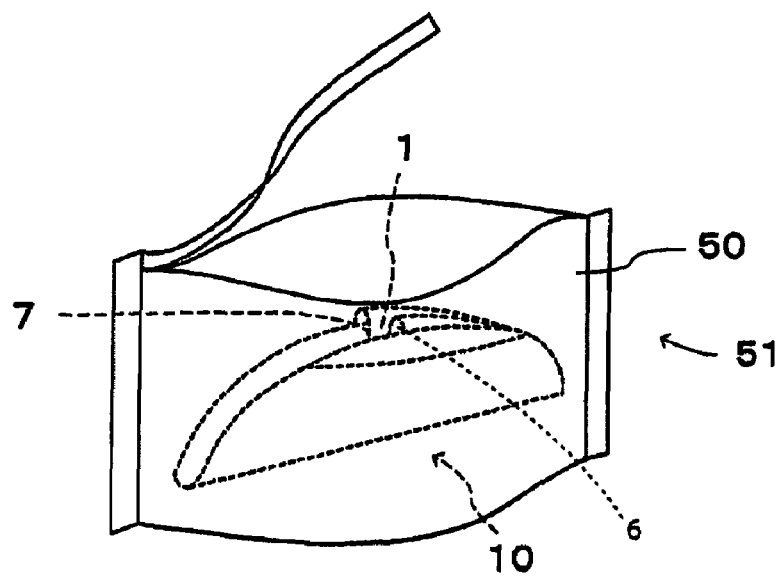
FIG. 27 is a schematic perspective view showing a wrapping body where the interlabial pad indicated with broken lines is folded to be contained in such a way that the finger insertion opening will open when unsealing the wrapping container.
Figure 28:
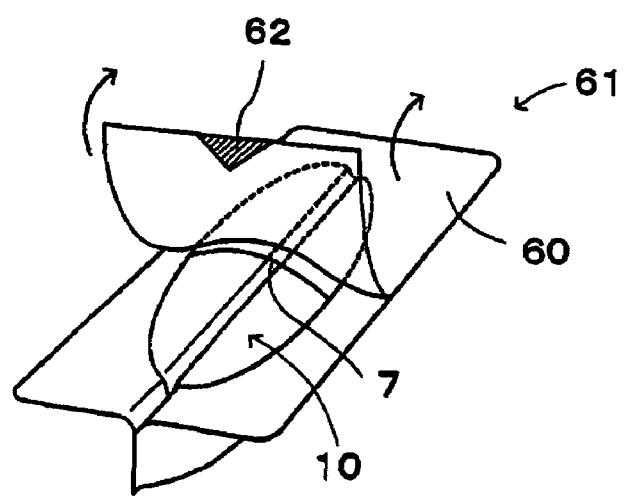
FIG. 28 is a schematic perspective view showing the state that a wrapping container marked with a sign indicating an unsealing direction aligned to the inserting direction of a finger inserted into the finger insertion opening of the interlabial pad contained therein is unsealed.
Figure 29:
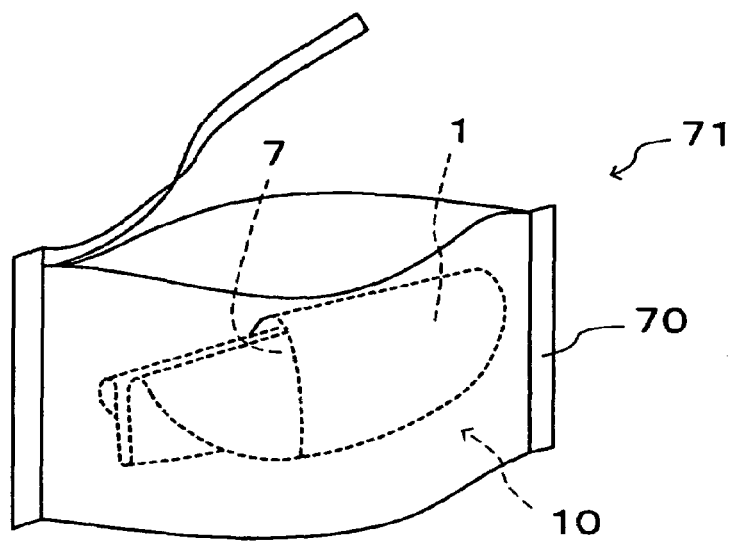
FIG. 29 is a schematic perspective view showing the state that a wrapping body where the mini sheet piece of the interlabial pad indicated with broken lines is folded facing outward in the shape plumping towards body is unsealed.
Figure 30:
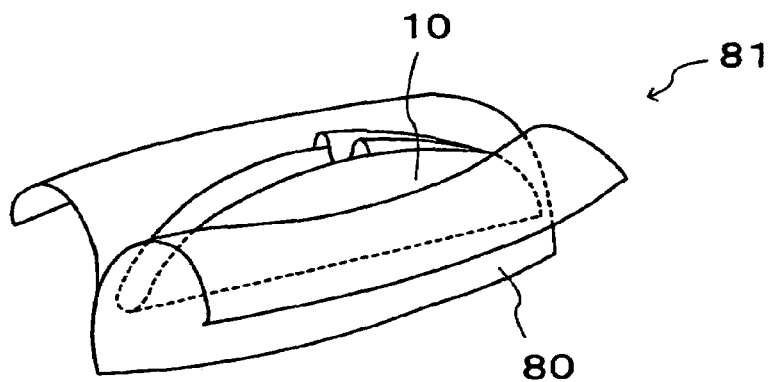
FIG. 30 is a schematic perspective view showing a wrapping body that is unsealed like opening a set of folded doors until the interlabial pad contained in a wrapping container is exposed.
Figure 31:
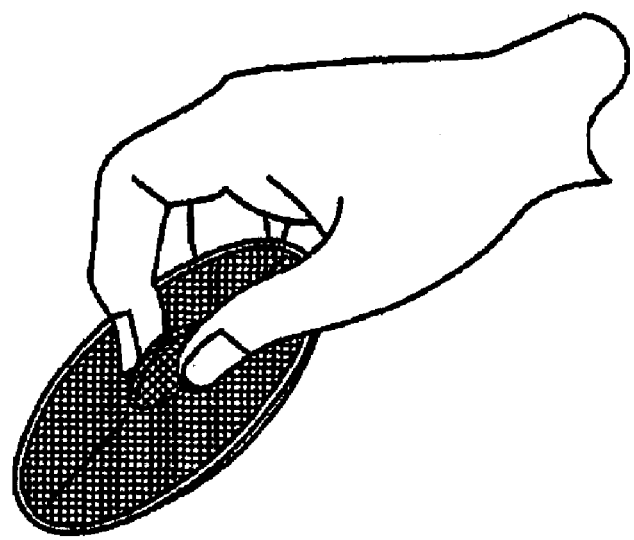
FIG. 31 is a diagram showing the use condition of a conventional example with a projection on the reverse side of the interlabial pad.

The wrapping body to wrap the interlabial pad according to the example in a wrapping container will now be explained. FIG. 27 is a schematic is perspective view showing a wrapping body 51 where the interlabial pad 10 indicated with broken lines is folded and contained in such a way that the finger insertion opening 7 will open when unsealing the wrapping container 50. FIG. 28 is a schematic perspective view showing the state that a wrapping body 61 is unsealed where the wrapping container 60 has a sign indicating an unsealing direction that is the same as the direction of a finger inserted into the finger insertion opening 7 of the interlabial pad 10 contained therein. FIG. 29 is a schematic perspective view showing the state that the wrapping body 71 is unsealed, where the mini sheet piece 7 of the interlabial pad 10 denoted by broken lines is folded right side out with the shape plumping towards the body-facing side. FIG. 30 is a schematic perspective view showing the state that the wrapping body 81 is unsealed, where the wrapping container 80 is opened like a set of folding doors until the interlabial pad contained in the wrapping container 80 is exposed.

The interlabial pad 10 according to the example of the present invention may be, as shown in FIG. 27, wrapping body 51 contained in the wrapping container 50. This kind of wrapping body 51 can be carried one by one since the interlabial pads 10 are wrapped independently. So, it is possible to handle them cleanly and conveniently compared to the case where multiple interlabial pads are contained in a single wrapping container.

In addition to that, in the wrapping body 51, the interlabial pad 10 is contained in the wrapping container 50 in such a way that the finger insertion opening 7 is opened toward the unsealing opening. "In such a way that the finger insertion opening 7 is opened toward the unsealing opening" shown above denotes, as shown in FIG. 27, the state that the interlabial pad 10 is contained in such a way that the mini sheet piece 1 and the finger insertion opening 7 formed by the same are exposed at the unsealing opening of the wrapping body 51 and a finger can be inserted into it immediately when the wrapping body 51 is opened. For example, the unsealing opening of the wrapping container 50 in the wrapping body 51 is formed with perforations. It can be opened by pulling it from the backside to front side of the drawing. Then, the finger insertion opening 7 is exposed at the unsealing opening and opened towards the unsealing opening. So, a wearer can insert a finger into the finger insertion opening 7 immediately.

In this case, the wrapping body 51 is preferably constructed in such a way that it can be opened from only one direction, or as shown in FIG. 28, the wrapping container 60 is preferably marked with a sign 62 to indicate the opening direction. By these manners, the opening direction and the finger insertion opening 7 are aligned to the same direction and a wearer can insert a finger into the finger insertion opening 7 more quickly since the finger insertion opening 7 is always made to face a wearer.

Further, as shown in FIG. 29, the wrapping body 71 may be constructed in such a way that the mini sheet piece 1 is contained in the wrapping container 70 and mountain folded towards the opposite side of body along the substantial center line of the interlabial pad 10 in the longitudinal direction. By containing the interlabial pad 10 in the wrapping container 70, it is possible for a wearer to easily identify the position to which a finger is inserted and wear the interlabial pad 10 more speedily and easily since the finger insertion opening 7 that is folded opens by itself when opening the wrapping container 70. Opening methods of the wrapping container are not particularly limited. Methods usable include, as shown in FIGS. 27 and 29, that a wrapping container is opened by cutting off the top edge, or as shown in FIG. 30, that the wrapping container 80 is opened by unsealing the top edge like opening a set of folding doors to take out the interlabial pad 10.

As explained above, when a wearer wear the interlabial pad, a finger inserted into the finger insertion opening from the finger insertion opening, stays at the finger insertion restriction portion in the finger insertion opening. So, it becomes possible to stably hold the positional relationship between a ball of a finger in the top joint (fingerprint side) and the interlabial pad in the longitudinal direction, and to reduce the positional displacement against the labia when wearing the pad, further identify the fixing position of the interlabial pad more accurately by detecting the position of the ostium vaginae with a ball of a finger in the top joint having superior sensitivity.

What is claimed is:

1. An interlabial pad for absorbing body fluid having a substantially rectangular shape comprising:
    a face adapted to face a body;
    an opposite face adapted to face a garment;
    said substantially rectangular-shaped pad having opposing first and second terminal end edges in a longitudinal direction of the interlabial pad;
    a cavity for finger insertion formed along the longitudinal direction of the interlabial pad on the opposite face, the cavity being formed between the opposite face and a mini-sheet; the mini-sheet having a first terminal end edge and a second terminal end edge in the longitudinal direction of the interlabial pad, wherein the mini-sheet is directly attached to a portion of the opposite face; and
    a cavity opening formed from the first terminal end edge of the mini-sheet for guiding a fingertip of a wearer inserted therein toward a finger restriction portion formed at an opposing end of the cavity and adapted to stop the fingertip inserted therein, the opposing end of the cavity being at a position displaced from the second terminal end edge of the mini-sheet toward the first terminal end edge of the mini-sheet;
    wherein the mini-sheet extends from one lateral side to another lateral side of the interlabial pad and has a total length from the first terminal end edge thereof to the second terminal end edge thereof in the longitudinal direction of 50% to 80% of an entire length of the interlabial pad from the first terminal end edge of the pad to the second terminal end edge of the pad;
    wherein the mini-sheet extends in the longitudinal direction from a position displaced from the second terminal end edge of the interlabial pad to an intermediate position along the longitudinal direction between the first and second terminal end edges of the interlabial pad;
    wherein a cross-sectional area of the cavity is gradually narrowed along the longitudinal direction of the interlabial pad in a direction proceeding from the first terminal end edge toward the second terminal end edge of the interlabial pad, such that the fingertip that is inserted can be stopped;
    wherein the finger restriction portion is defined by two facing portions of a fold formed in the opposite face, the fold extending in a longitudinal direction from the first terminal end edge to the second terminal end edge of the interlabial pad;
    wherein the two facing portions include respective portions which are substantially parallel to each other in a plane that is substantially perpendicular to a plane extending through the crest of the fold from the opposite face to the face adapted to face the body, the two facing portions being directly bonded to each other at respective locations thereof juxtaposed to said plane extending through said crest;
    wherein the fold formed in the opposite face forms a portion protruding from a remaining portion of the face adapted to face the body, and the remaining portion forms a first planar portion at one side of the protruding portion and a second planar portion at another side of the protruding portion which portions are substantially parallel to one another and parallel with and opposite to the respective portions of the two facing portions;
    wherein the protruding portion is coextensive with the fold.

2. The interlabial pad according to claim 1, wherein an interval dimension between the cavity opening for finger insertion and said finger restriction portion is 10% to 80% of the entire length in the longitudinal direction of the interlabial pad.

3. The interlabial pad according to claim 1, wherein the cavity opening formed from the first terminal end edge of the mini-sheet is disposed at a location that is 40% from the first end edge along the longitudinal direction of the interlabial pad, and wherein said finger restriction portion is disposed at a location that is 90% from the first end edge along the longitudinal direction of the interlabial pad.

4. The interlabial pad according to claim 3, wherein the entire length of the interlabial pad in the longitudinal direction is between 50 mm and 160 mm.

5. The interlabial pad according to claim 4, wherein the entire length of the interlabial pad in the longitudinal direction is between 80 mm and 130 mm.

6. The interlabial pad according to claim 1, wherein the interlabial pad is used together with a sanitary napkin.

7. The interlabial pad according to claim 1, wherein said interlabial pad is for incontinence.

8. The interlabial pad according to claim 1, wherein said interlabial pad is for absorbing vaginal discharge.

9. The interlabial pad according to claim 1, wherein the mini-sheet is attached in direct contact with the respective portions of the two facing portions formed in the opposite face opposite to the respective first planar portion and the second planar portion.

10. The interlabial pad according to claim 1, wherein the interlabial pad comprises one or more of a biodegradable material, a water-soluble material, and a water-dispersible material.

* * * * *